(12) United States Patent
Lim et al.

(10) Patent No.: US 9,732,120 B2
(45) Date of Patent: Aug. 15, 2017

(54) SELF-ASSEMBLED PEPTIDE NANOSTRUCTURES BY EXPLOITING CONFORMATIONAL CHANGE, BIOSENSOR USING THE SAME AND DETECTION METHOD OF BIOMOLECULES USING THE SAME

(71) Applicant: INDUSTRY-ACADEMIC COOPERATION FOUNDATION, YONSEI UNIVERSITY, Seoul (KR)

(72) Inventors: Yong-beom Lim, Seoul (KR); So-hee Han, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/712,184

(22) Filed: May 14, 2015

(65) Prior Publication Data
US 2016/0084829 A1    Mar. 24, 2016

(30) Foreign Application Priority Data

May 14, 2014  (KR) ........................ 10-2014-0057852

(51) Int. Cl.
*C07K 14/00* (2006.01)
*A61B 5/00* (2006.01)
(Continued)

(52) U.S. Cl.
CPC .......... *C07K 14/001* (2013.01); *A61B 5/0071* (2013.01); *C07K 7/06* (2013.01);
(Continued)

(58) Field of Classification Search
None
See application file for complete search history.

(56) References Cited

FOREIGN PATENT DOCUMENTS

| KR | 10-2009-0093674 | 9/2009 |
| KR | 10-2009-0093684 | 9/2009 |

OTHER PUBLICATIONS

Sambasivan et al. Determination of orientational isomerism in rhodium(II) metallopeptides by pyrene fluorescence. Org. Biomol. Chem., 2012, 10, 8203-8206.*

(Continued)

*Primary Examiner* — Satyanarayana R Gudibande
*Assistant Examiner* — Jia-Hai Lee
(74) *Attorney, Agent, or Firm* — Duane Morris LLP; J. Rodman Steele, Jr.; Gregory M. Lefkowitz

(57) ABSTRACT

The present disclosure relates to a self-assembled peptide nanostructure including at least one amphiphilic peptide and a biosensor using the same. The amphiphilic peptide is a hairpin-shaped amphiphilic peptide including a hydrophilic domain having an α-helical structure and a hydrophobic domain. The N-terminal of the hydrophobic domain is a pyrene group. Since the self-assembled peptide nanostructure is derived from an RNA, DNA or amino acid sequence capable of recognizing a specific target substance, it does not recognize other substances but exhibits high selectivity for the target substance. Specifically, since the self-assembled peptide nanostructure has an excimer fluorescence peak at 480 nm through binding with the target substance, it can be usefully used in medical applications such as diagnosis of diseases.

14 Claims, 23 Drawing Sheets

(51) Int. Cl.
  *G01N 33/52* (2006.01)
  *G01N 33/542* (2006.01)
  *C07K 7/06* (2006.01)
  *C07K 7/08* (2006.01)
  *C09B 62/00* (2006.01)
  *H01L 51/00* (2006.01)

(52) U.S. Cl.
  CPC ............... *C07K 7/08* (2013.01); *G01N 33/52* (2013.01); *G01N 33/542* (2013.01); *B01L 2300/0636* (2013.01); *C09B 62/00* (2013.01); *H01L 51/0054* (2013.01)

(56) References Cited

OTHER PUBLICATIONS

Han et al. Bioinspired Self-Assembled Peptide Nanofibers with Thermostable Multivalent α Helices. Biomacromolecules 2013, 14, 1594-1599.*
Nongonierma et al. Inhibition of dipeptidyl peptidase IV (DPP-IV) by tryptophan containing dipeptides. Food Funct., 2013, 4, 1843.*
Christen et al. Prion Protein mPrP[F175A](121-231): Structure and Stability in Solution. J. Mol. Biol. (2012) 423, 496-502.*
Thirunavukkuarasu et al. Multiparametric Fluorescence Detection of Early Stages in the Amyloid Protein Aggregation of Pyrene-labeled α-Synuclein. J. Mol. Biol. (2008) 378, 1064-1073.*

* cited by examiner

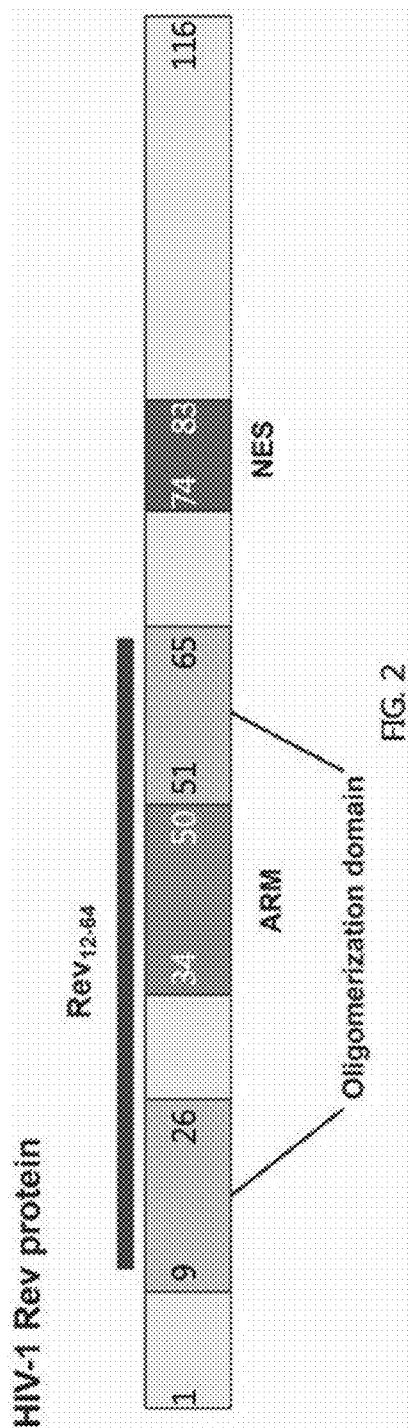

SELF-ASSEMBLED PEPTIDE NANOSTRUCTURES BY EXPLOITING CONFORMATIONAL CHANGE, BIOSENSOR USING THE SAME AND DETECTION METHOD OF BIOMOLECULES USING THE SAME

CROSS-REFERENCE TO RELATED APPLICATIONS

This application claims priority under 35 U.S.C. §119 to Korean Patent Application No. 10-2014-0057852 filed on May 14, 2014 in the Korean Intellectual Property Office, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 23, 2015, is named G1035-05401_SL.txt and is 2,277 bytes in size.

TECHNICAL FIELD

The present disclosure relates to a self-assembled peptide nanostructure, more particularly to a peptide nanostructure which undergoes conformational change and emits fluorescence when a target substance is bound to a recognition site of the peptide nanostructure, a biosensor which is capable of detecting the target substance by exploiting the same and a detection method using the same.

BACKGROUND

A biosensor refers to a system which transforms the information of a target substance to a recognizable, useful signal. It is a device which consists of a bioreceptor and a signal transducer and selectively detects the substance to be analyzed by transforming the information of the target substance to a recognizable signal. It is very important not only in medical applications for diagnostic purposes but also in basic medical studies of the mechanisms of various biological responses.

Since high selectivity and sensitivity for a specific target substance are required for the biosensor, an effective mechanism should be ensured between the bioreceptor and the signal transducer. For instance, although a biosensor using an enzyme and an antibody has excellent substrate specificity and binding affinity, it is unsatisfactory in terms of stability and cost.

Recently, development of a high-sensitivity fluorescence biosensor using a supramolecular compound and a fluorescent material, which allows for detection of selective binding to a target substance based on change in fluorescence, is drawing a lot of attentions.

In this regard, a variety of fluorescence sensors for detecting cationic, anionic and neutral organic molecules have been developed. These are interesting techniques providing high detection limit and simple operation by detecting fluorescence signals based on changes induced by anionic compounds. In particular, a fluorescence sensor exhibiting selectivity for pyrophosphate (PPi), which plays an important role in signaling and energy storage in biological systems, is advantageous in that it emits fluorescence by the chelate enhanced fluorescence (CHEF) effect upon reaction with a specific anionic compound in the presence of copper ion (patent documents 1 and 2). However, these methods require numerous trials and errors and are time-consuming.

To solve these problems, development of a biosensor which can detect a specific target substance faster and more effectively with high sensitivity is urgently needed.

REFERENCES OF THE RELATED ART

Patent Documents

Patent document 1. Korean Patent Publication No. 10-2009-0093684
Patent document 2. Korean Patent Publication No. 10-2008-0093674

SUMMARY

The present disclosure is directed to providing a self-assembled peptide nanostructure which selectively binds to a target substance.

The present disclosure is also directed to providing a biosensor which effectively detects a target substance and a detection method using the same.

In an aspect, the present disclosure provides a self-assembled peptide nanostructure including at least one amphiphilic peptide, wherein the amphiphilic peptide includes a first hydrophobic oligomerization domain, a hydrophilic α-helix domain and a second hydrophobic oligomerization domain sequentially from the N-terminal to the C-terminal, and the N-terminal of the first hydrophobic oligomerization domain is a pyrene group.

The amphiphilic peptide may be a hairpin-shaped amphiphilic peptide wherein the first and second hydrophobic oligomerization domains are faced to each other.

The peptide nanostructure may be formed as a globular peptide nanostructure from self-assembly of the hairpin-shaped amphiphilic peptide.

The peptide nanostructure may have an average particle diameter of 20-70 nm.

The hydrophilic α-helix domain may include an arginine-rich motif (ARM) and a proline-rich loop forming an α-helical structure.

The arginine-rich motif may be derived from the 34th through 50th amino acid sequence of the HIV-1 rev protein.

The arginine-rich motif may include an amino acid sequence of [SEQ ID NO 1].

[SEQ ID NO 1]
TRQARRNRRRRWERQR

The proline-rich loop may include an amino acid sequence of [SEQ ID NO 2].

[SEQ ID NO 2]
GEPNPPP

The first and second hydrophobic oligomerization domains may be derived respectively from the 9th through 26th or 51st through 65th amino acid sequence of the HIV-1 rev protein.

The first and second hydrophobic oligomerization domains may respectively include an amino acid sequence of [SEQ ID NO 3] or [SEQ ID NO 4].

QIHSISERILSTYLK [SEQ ID NO 3]

NSQYLFKILRVAKLL [SEQ ID NO 4]

The peptide nanostructure may maintain the shape of the peptide nanostructure from self-assembly of the amphiphilic peptide when the ionic strength is 0.1-0.3 M.

In another aspect, the present disclosure provides a biosensor using the peptide nanostructure.

The peptide nanostructure may have a stabilized (folded) α-helical structure by binding with a target substance and fluorescence emission may be changed depending on the distance between pyrene groups in the stabilized peptide nanostructure.

The biosensor may detect a target substance under an ionic strength of 0.1-0.3 M.

The target substance may be selected from a group consisting of an amino acid, a protein, an RNA and a DNA to which the hydrophilic α-helix domain of the peptide nanostructure binds selectively.

The target substance may be HIV-1 RRE RNA. More specifically, the hydrophilic domain of the peptide nanostructure may recognize and bind to the stem-loop II of the HIV-1 RRE RNA.

In another aspect, the present disclosure provides a detection method using a biosensor, including:

I) contacting a sample containing a target substance with the biosensor; and

II) detecting the target substance by measuring the fluorescence intensity of the biosensor.

Since the self-assembled peptide nanostructure according to the present disclosure is derived from an RNA, DNA or amino acid sequence capable of recognizing the target substance, it does not recognize other substances but exhibits high selectivity for the target substance. Specifically, since the self-assembled peptide nanostructure has an excimer fluorescence peak at 480 nm through binding with the target substance, it can be usefully used in medical applications such as diagnosis of diseases.

BRIEF DESCRIPTION OF DRAWINGS

FIG. 2 schematically shows the domain structure of the HIV-1 rev protein consisting of 116 amino acid residues. The amino acid residues 9 to 26 and 51 to 65 indicate hydrophobic oligomerization domains and amino acid residues 34 to 50 indicate an arginine-rich motif (ARM) including an α-helical structure.

FIG. 15a is a height image and FIG. 15b is a phase image.

FIG. 16a is a height image and FIG. 16b is a phase image.

FIG. 19a is a height image and FIG. 19b is a phase image.

FIG. 20a is a height image and FIG. 20b is a phase image.

μM) to investigate whether the self-assembled peptide nanostructure of the present disclosure can detect a target substance.

Figure 22:
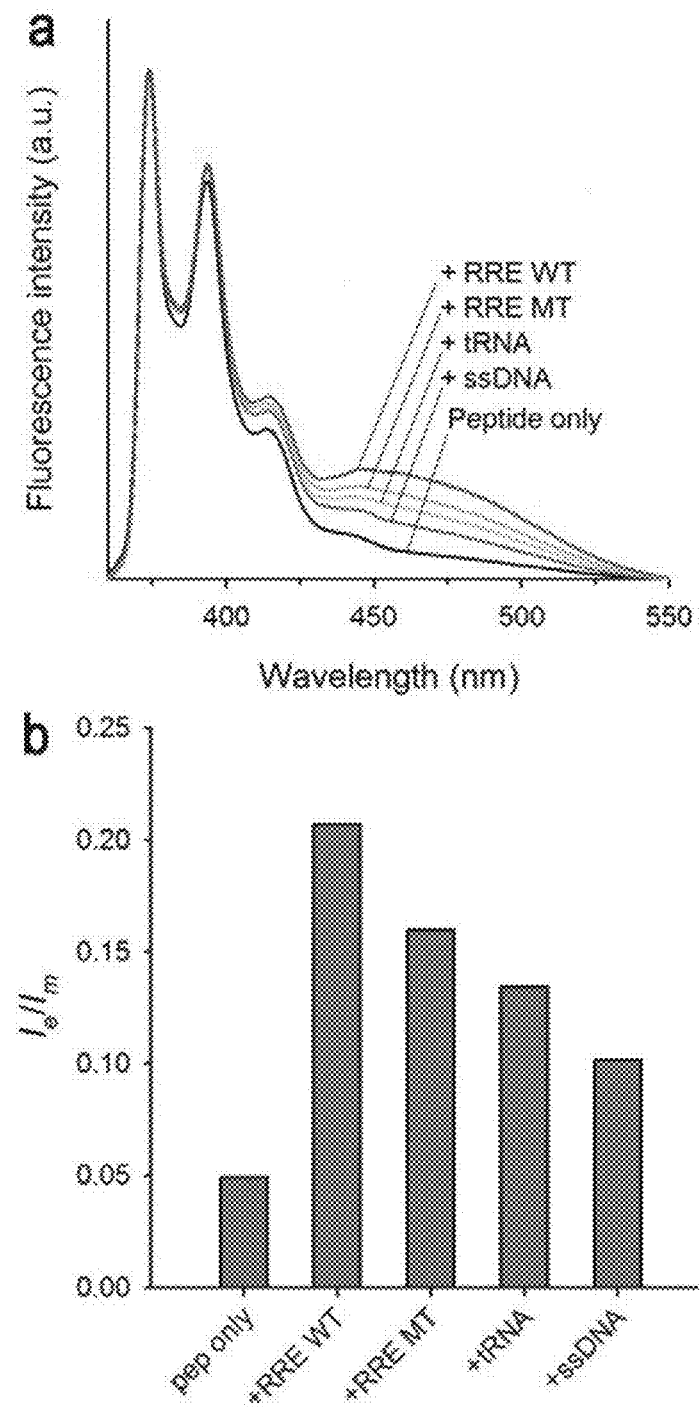

FIG. 22 shows a fluorescence spectroscopic analysis result of a self-assembled peptide nanostructure prepared in Example after mixing with various biomolecules.

Figure 23A:
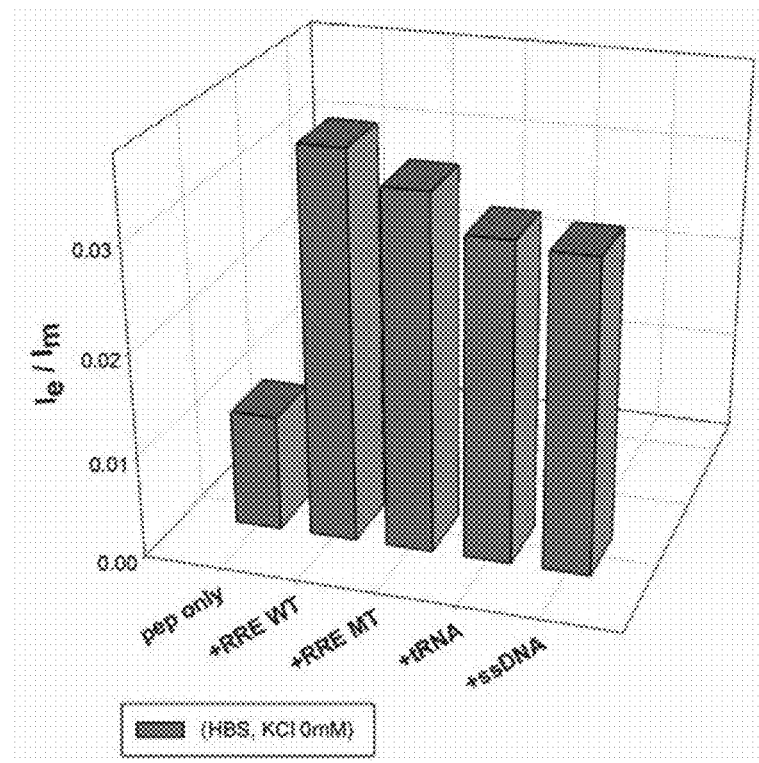
Figure 23B:
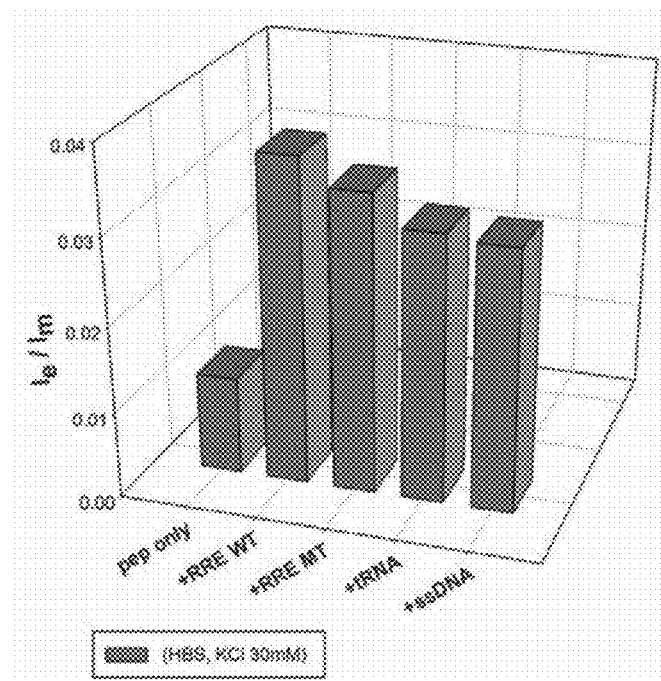
Figure 23C:
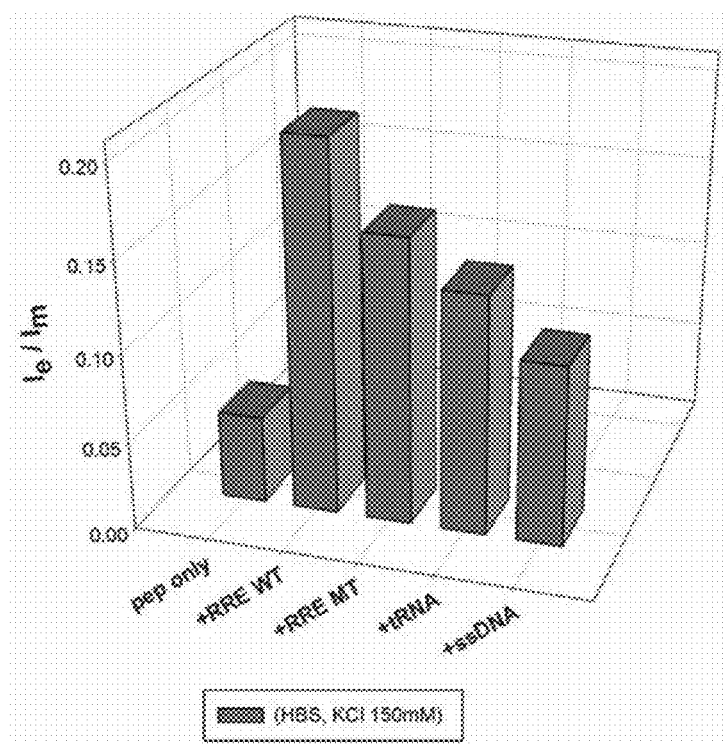

FIGS. 23a-23c shows a fluorescence spectroscopic analysis result of a self-assembled peptide nanostructure prepared in Example under different ionic strengths after mixing with various biomolecules.

DETAILED DESCRIPTION OF EMBODIMENTS

Hereinafter, various aspects and exemplary embodiments of the present disclosure will be described in further detail.

In the present disclosure, the term 'self-assembly' includes assembly induced by non-covalent bondings (hydrogen bonding, ionic bonding, van der Waals bonding, hydrophobic bonding, electrostatic bonding, etc.). In the present disclosure, a peptide is used as a substance capable of self-assembly.

In the present disclosure, the term 'excimer' refers to a dimer formed from two molecular species, one in the ground state and the other in the excited state, spatially adjacent to each other. It can exist stably only in the excited state because the total system is stabilized as excitation energy and charge are transferred from one to the other. Although its absorption spectrum cannot be observed because it is dissociated in the ground state, it can exhibit a specific fluorescence intensity.

Figure 1:
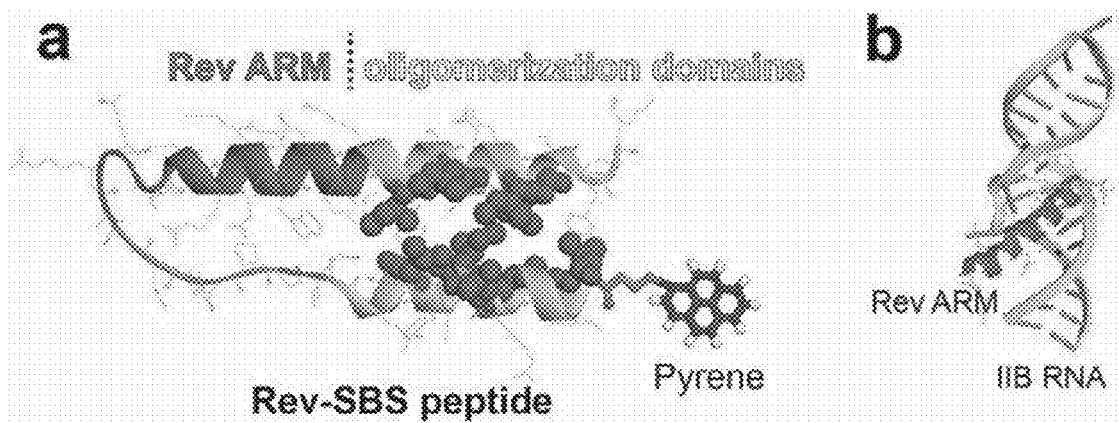
FIG. 1 is a schematic diagram for explaining the structure (a) and function (b) of an amphiphilic peptide constituting a self-assembled peptide nanostructure according to the present disclosure.

In an aspect, the present disclosure provides a self-assembled peptide nanostructure including at least one amphiphilic peptide, wherein the amphiphilic peptide includes a first hydrophobic oligomerization domain, a hydrophilic α-helix domain and a second hydrophobic oligomerization domain sequentially from the N-terminal to the C-terminal, and the N-terminal of the first hydrophobic oligomerization domain is a pyrene group, the structure and function of which are shown in FIG. 1 and FIG. 2.

Figure 3A:
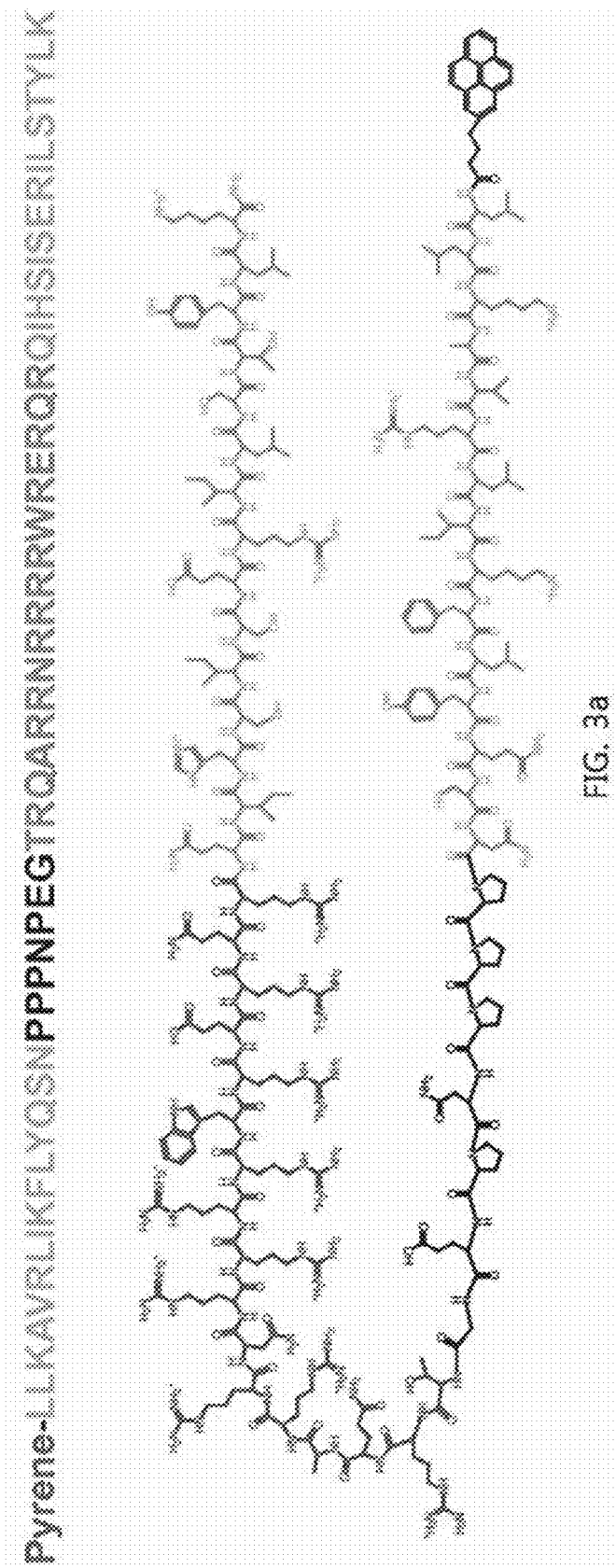
FIG. 3a schematically shows the chemical structure and sequence of an amphiphilic peptide (SEQ ID NO: 8) constituting a self-assembled peptide nanostructure according to the present disclosure.
Figure 3B:
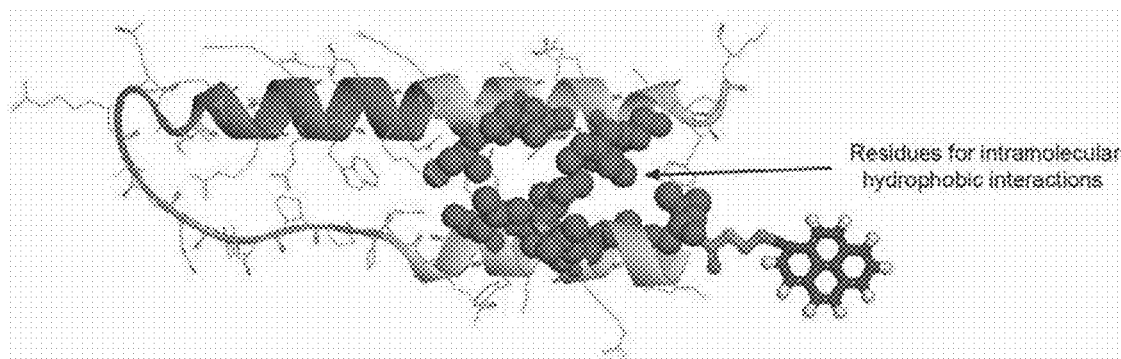
FIG. 3b shows the X-ray crystallographic structure of a pyrene-bound amphiphilic peptide constituting a self-assembled peptide nanostructure according to the present disclosure.
Figure 3C:
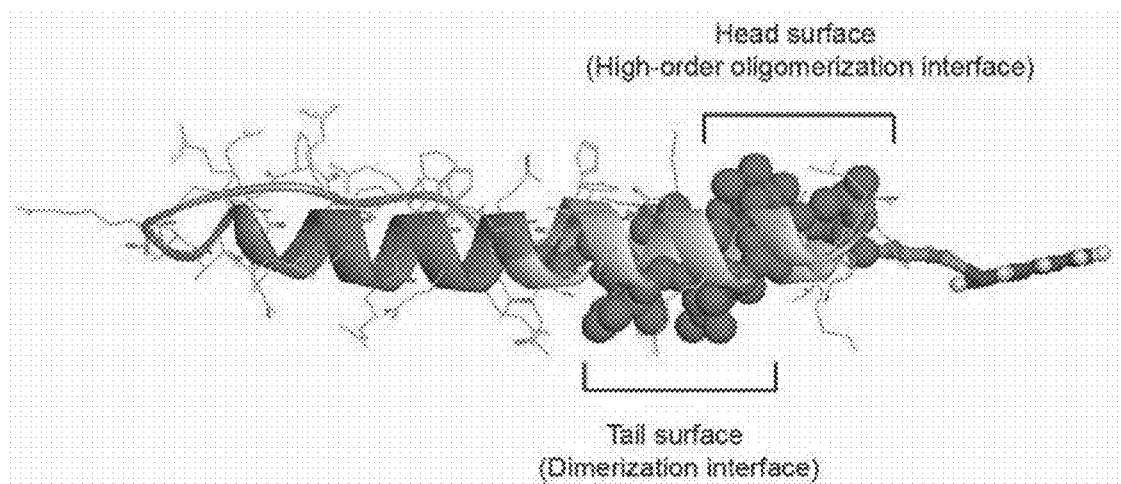
FIG. 3c shows the amphiphilic peptide constituting a self-assembled peptide nanostructure according to the present disclosure in FIG. 3b rotated by 90°.

FIG. 1 is a schematic diagram for explaining the structure (a) and function (b) of the amphiphilic peptide constituting the self-assembled peptide nanostructure according to the present disclosure. FIG. 2 schematically shows the domain structure of the HIV-1 rev protein consisting of 116 amino acid residues, wherein the amino acid residues 9 to 26 and 51 to 65 indicate hydrophobic oligomerization domains, amino acid residues 34 to 50 an arginine-rich motif (ARM) including an α-helical structure and the bar marked Rev$_{12-64}$ indicates the amphiphilic peptide used in the self-assembled peptide nanostructure according to the present disclosure. FIG. 3a schematically shows the chemical structure and sequence of the amphiphilic peptide constituting the self-assembled peptide nanostructure according to the present disclosure. FIG. 3b shows the X-ray crystallographic structure of the amphiphilic peptide constituting the self-assembled peptide nanostructure according to the present disclosure. FIG. 3c shows the amphiphilic peptide constituting the self-assembled peptide nanostructure according to the present disclosure in FIG. 3b rotated by 90°.

As shown in the figures, the amphiphilic peptide of the self-assembled peptide nanostructure of the present disclosure, which can be used to detect a target substance, includes the first hydrophobic oligomerization domain, the hydrophilic α-helix domain and the second hydrophobic oligomerization domain sequentially from the N-terminal to the C-terminal, and the N-terminal of the first hydrophobic oligomerization domain is a pyrene group. The amphiphilic peptide has a hairpin-shaped structure.

The hydrophilic α-helix domain may include the whole or part of a target substance recognition site that can specifically bind to or recognize the target substance. For example, it may include part of an amino acid sequence corresponding to the target substance. Hereinafter, the hydrophilic α-helix domain is described in more detail.

The hydrophilic α-helix domain may contain an arginine-rich motif (ARM) and a proline-rich loop forming an α-helical structure. Specifically, the arginine-rich motif may be derived from the 34th through 50th amino acid sequence of the HIV-1 rev protein. More specifically, the arginine-rich motif may include an amino acid sequence of [SEQ ID NO 1] and the proline-rich loop may include an amino acid sequence of [SEQ ID NO 2].

[SEQ ID NO 1]
TRQARRNRRRRWERQR

[SEQ ID NO 2]
GEPNPPP

The first and second hydrophobic oligomerization domains are connected to both ends of the hydrophilic α-helix domain of the amphiphilic peptide and allow for the formation of a hairpin structure through hydrophobic interactions between amino acid molecules. Particularly in the present disclosure, they may consist of or include oligomerization domains.

More specifically, the first and second hydrophobic oligomerization domains may be derived respectively from the 9th through 26th or 51st through 65th amino acid sequence of the HIV-1 rev protein. More specifically, the first and second hydrophobic oligomerization domains may respectively include an amino acid sequence of [SEQ ID NO 3] or [SEQ ID NO 4].

[SEQ ID NO 3]
QIHSISERILSTYLK

[SEQ ID NO 4]
NSQYLFKILRVAKLL

Above a specific ionic strength, the amphiphilic peptide having the structure described above forms a V-shaped dimer through interaction of tail to tail surface present on the first and second hydrophobic oligomerization domains of the amphiphilic peptide, i.e. head-to-head, tail-to-tail non-covalent bonding, as seen from FIG. 3c. As a result of binding between the hydrophobic higher order oligomerization domains of the dimers, a peptide nanostructure is formed through self-assembly.

Although the amphiphilic peptide that has formed the V-shaped dimer may exhibit affinity for another stem-loop through protein-protein or protein-RNA interaction, the involved fluorescence intensity is very low and, thus, it is distinguishable from the binding with the target substance. This is demonstrated in Test Examples.

Figure 4:
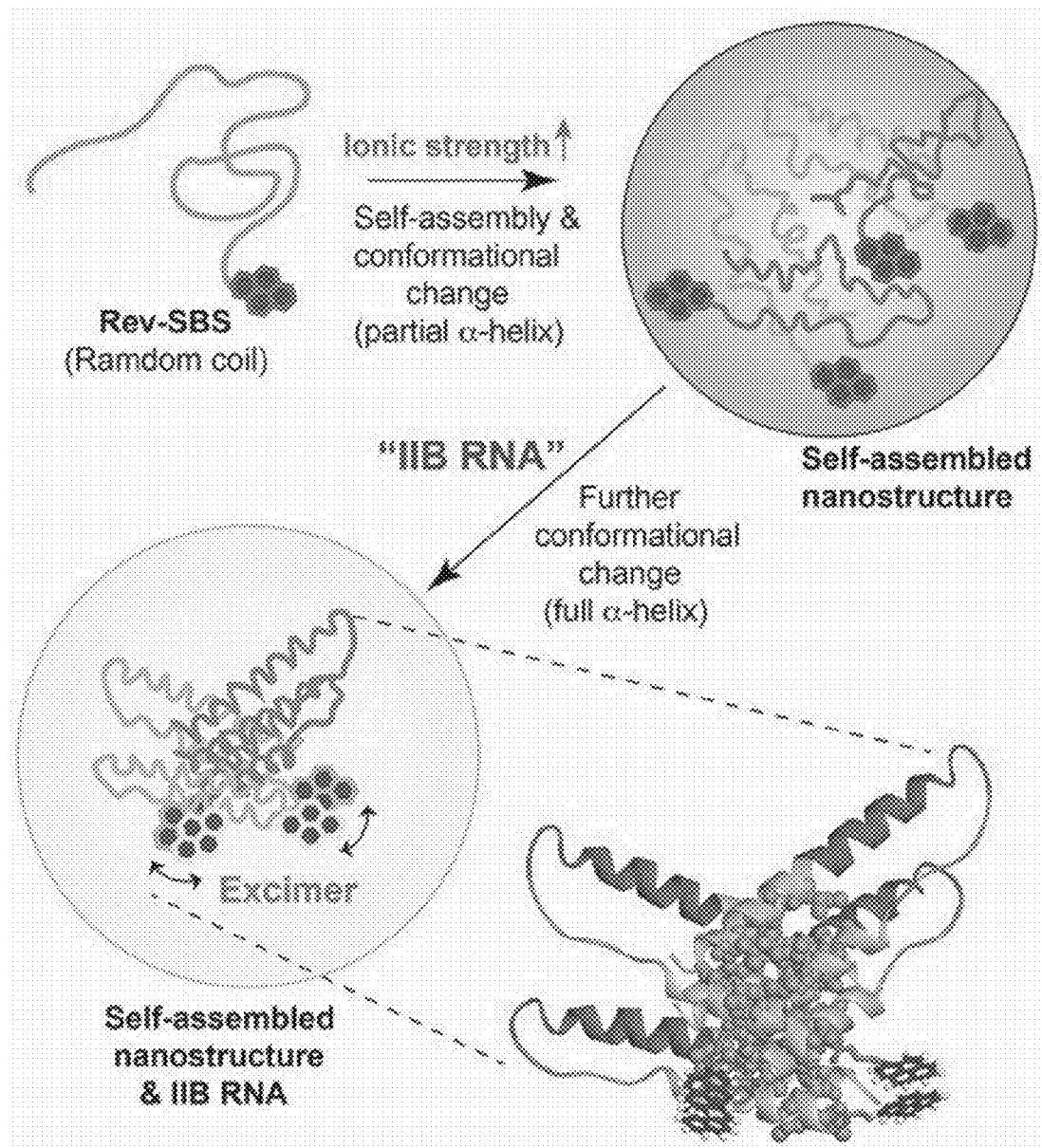
FIG. 4 is a schematic diagram for explaining a method for detecting a target substance using a self-assembled peptide nanostructure according to the present disclosure.
Figure 5A:
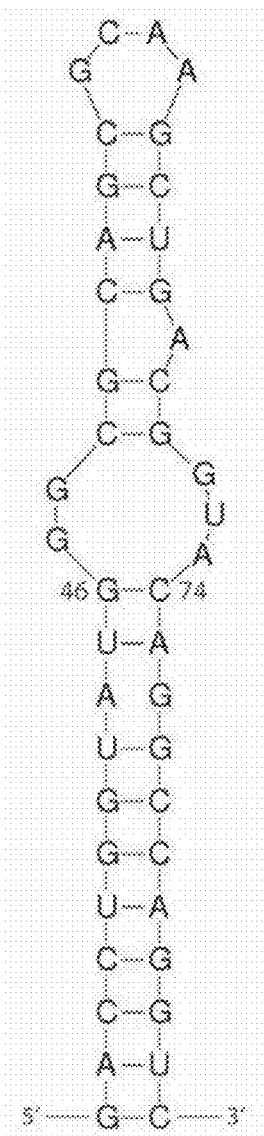
FIG. 5a shows the structure of HIV-1 RRE RNA (SEQ ID NO: 5) according to the present disclosure.
Figure 5B:
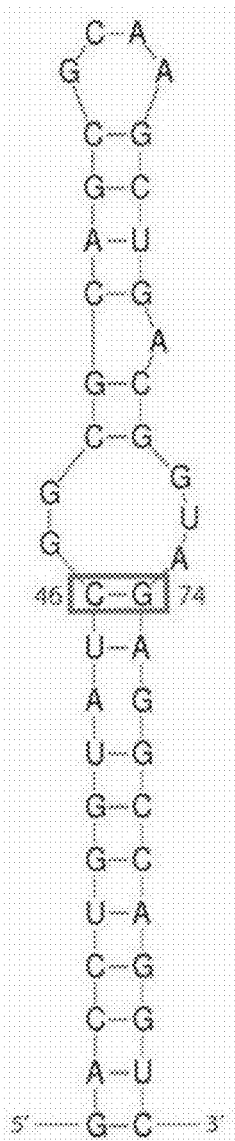
FIG. 5b shows the structure of an HIV-1 RRE RNA (SEQ ID NO: 6) mutant according to the present disclosure.

More specifically, the self-assembled peptide nanostructure has a globular shape as a result of binding between the dimers. This process is depicted in FIG. 4.

The ionic strength may be specifically 0.1 or higher, more specifically 0.1-0.3. If the ionic strength is lower than 0.1, a peptide nanostructure with a desired shape cannot be obtained because self-assembly of the amphiphilic peptide does not occur. And, if the ionic strength is higher than 0.3, the target substance cannot be detected as desired because the shape of the peptide nanostructure is changed.

Under a specific ionic strength condition, the self-assembled peptide nanostructure has a globular shape as a result of aggregation. However, the secondary structure, i.e., the α-helical structure, in the self-assembled peptide nanostructure is not completely stabilized (folded) but remains partially unfolded.

The degree of stabilization of the α-helical structure of the amphiphilic peptide in the peptide nanostructure can be expressed by the ratio of molar ellipticities at 222 nm and 208 nm ($[\theta]_{222}/[\theta]_{208}$) measured by circular dichroism (CD) spectroscopy. The peptide nanostructure not bound to the target substance has a $[\theta]_{222}/[\theta]_{208}$ of 0.45-0.7, indicating that the α-helical structure in the peptide nanostructure is in an unstabilized (unfolded) state.

In this state, the amphiphilic peptide in the self-assembled peptide nanostructure does not form an excimer because of the long distance between the pyrene groups and, thus, only emits monomer fluorescence at 373 nm.

However, if the self-assembled peptide nanostructure binds to the target substance, the α-helical structure in the self-assembled peptide nanostructure is significantly stabilized through conformational change and an excimer is formed by the pyrene groups of the amphiphilic peptides which are spatially adjacent to each other, which fluoresces at about 480 nm.

In this state where the α-helical structure of the self-assembled peptide nanostructure is stabilized, the $[\theta]_{222}/[\theta]_{208}$ is 1.1-2.0.

The target substance can be detected based on the principle, as illustrated in FIG. 4.

More specifically, the self-assembled peptide nanostructure of the present disclosure may selectively form an excimer and allow for detection at about 480 nm. Although the existing general sensor can detect a target substance based on the change in fluorescence intensity, the detection is significantly affected by the surrounding environment.

Accordingly, the present disclosure provides a biosensor using the self-assembled peptide nanostructure, which emits fluorescence as a result of conformational change induced by binding with the target substance.

The biosensor can detect the target substance by measuring the ratio of fluorescence intensities at two different wavelengths without being affected by environmental factors and can also estimate the concentration of the target substance.

In addition, the biosensor allows for effective detection of the target substance fast and easily because the detection of the target substance exploiting the conformational change of the peptide through self-assembly does not require complicated operation.

The target substance may be a biomolecule selected from a group consisting of a protein, an RNA and a DNA and may be different depending on the peptide included in the biosensor. Specifically, it may be HIV-1 RRE RNA, T7 DNA, an HIV-1 RRE RNA variant or HIV-1 tRNA, more specifically an HIV-1 RRE RNA. The structure and sequence of the HIV-1 RRE RNA, the HIV-1 RRE RNA variant and the T7 DNA are shown in FIGS. 5*a* and 5*b* and Table 1.

TABLE 1

| | Sequence |
|---|---|
| HIV-1 RRE RNA | 5'-GACCUGGUAUGGGCGCAGCGCAAGCUGACG GUACAGGCCAGGUC-3' (SEQ ID NO: 5) |

TABLE 1-continued

| | Sequence |
|---|---|
| HIV-1 RRE RNA variant | 5'-GACCUGGUAUCGGCGCAGCGCAAGCUGACG GUAGAGGCCAGGUC-3' (SEQ ID NO: 6) |
| T7 DNA | 5'-TAATACGACTCACTATAGGACCTGG-3' (SEQ ID NO: 7) |

For example, if the amphiphilic peptide of the self-assembled peptide nanostructure includes the amino acid sequence derived from the HIV-1 rev protein, it recognizes HIV-1 RRE RNA as a target substance and binds thereto. Under an ionic strength of 0.1-0.3, no significant change in fluorescence emission is observed for the addition of other biomolecules, in particular the HIV-1 RRE RNA variant (mutated IIB RNA), whereas a significant selective increase in fluorescence is observed at 480 nm for the addition of HIV-1 RRE RNA due to excimer formation. Accordingly, the self-assembled peptide nanostructure according to the present disclosure may be usefully used as a fluorescence biosensor for selectively detecting the human immunodeficiency virus (HIV) in vivo.

The present disclosure also provides a detection method using a biosensor, including:

I) contacting a sample containing a target substance with the biosensor; and

II) detecting the target substance by measuring the fluorescence intensity of the biosensor.

The presence of a particular substance may be detected using the biosensor by monitoring the excimer-induced fluorescence increase at 480 nm.

Hereinafter, the present disclosure will be described in more detail through examples. However, the following examples are for illustrative purposes only and the scope and teaching of the present disclosure should not be construed as being limited by the examples. In addition, it will be obvious that those of ordinary skill can easily carry out the present disclosure based on the teaching of the present disclosure including the examples, even when specific experimental results are not provided, and such changes and modifications are within the scope of the appended claims.

In particular, although only diphenylalanine or Fmoc-diphenylalanine were used in the examples as precursors for the synthesis of a peptide nanostructure, it will be obvious to those of ordinary skill in the related art from the present disclosure that any peptide capable of self-assembly can be applied to a method according to the present disclosure.

Preparation Example

The peptide of to the present disclosure was synthesized as follows. First, the first amino acid Fmoc-Ser-OH of the peptide sequence of the present disclosure was synthesized on solid 2-chlorotrityl resin. The amino acids following the Fmoc-Ser-OH were synthesized through peptide bonding using the Tribute peptide synthesizer (Protein Technologies, Inc.). During the synthetic procedure, standard amino acid protecting groups were used.

In order to bind a pyrene group to the N-terminal of the prepared resin-bound amphiphilic peptide, after deprotecting the Fmoc group at the N-terminal of the amphiphilic peptide with 20% piperidine and then treating with O-(benzotriazol-1-yl)-N,N,N',N'-tetramethyluronium hexafluorophosphate (HBTU) and N,N-diisopropylethylamine (DI- PEA), the pyrene group was bound to the N-terminal α-amine of the amphiphilic peptide using pyrenebutyric acid.

Figure 6:
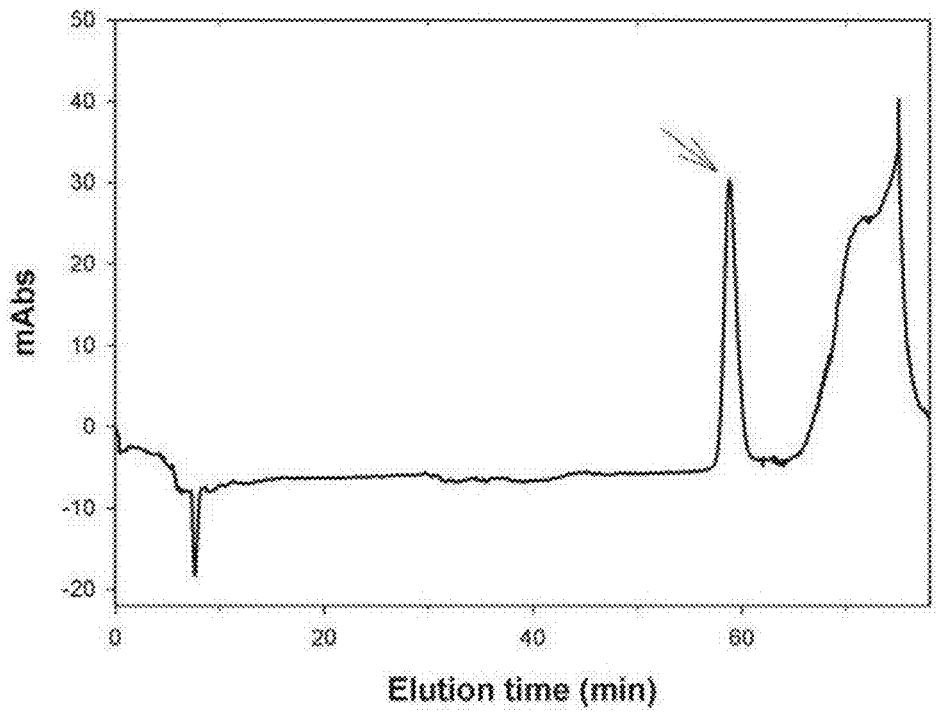
FIG. 6 shows an HPLC analysis result of an amphiphilic peptide prepared in Preparation Example.

Finally, in order to cleave the amphiphilic peptide from the resin, the resin-bound peptide was treated for 3 hours with a cleavage solution (trifluoroacetic acid (TFA)/triisopropylsilane (TIS)/water=95:2.5:2.5) and then prepared into powder using tert-butyl methyl ether. The obtained amphiphilic peptide was purified by reversed-phase HPLC (water-acetonitrile, 0.1% TFA) as shown in FIG. 6.

Figure 7:
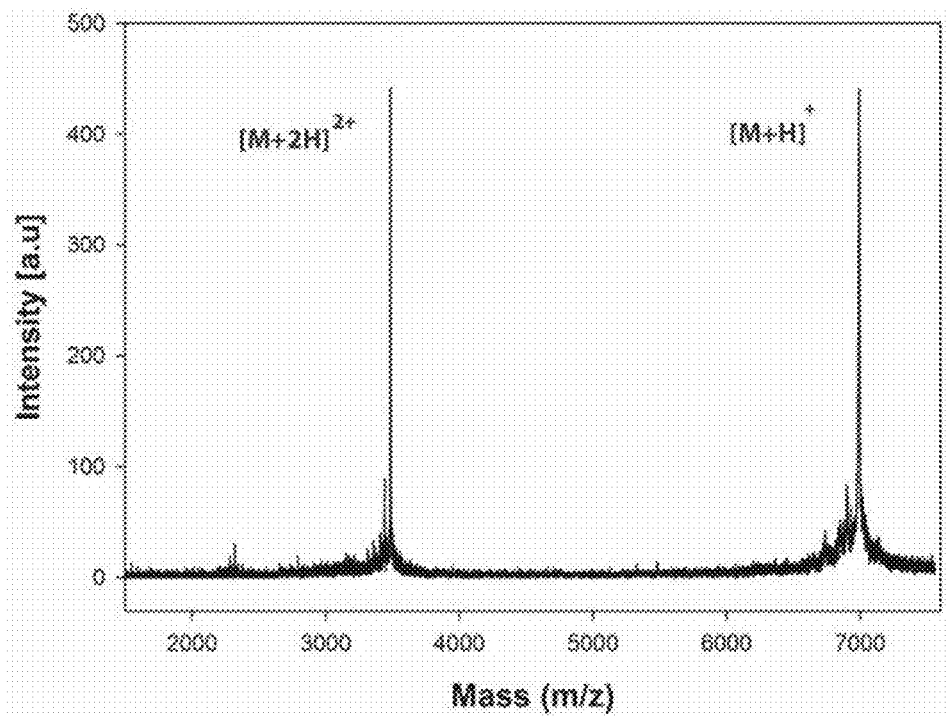
FIG. 7 shows a MALDI-TOF mass spectrum of an amphiphilic peptide prepared in Preparation Example.

The molecular weight of the purified amphiphilic peptide was measured by MALDI-TOF mass spectrometry. The result is shown in FIG. 7. In water/acetonitrile (1:1), the concentration of the synthesized peptide was determined spectroscopically at 341 nm by measuring the molar extinction coefficient of pyrene (38459 $M^{-1} \cdot cm^{-1}$).

EXAMPLE

The amphiphilic peptide prepared in Preparation Example was dissolved in a 150 mM KF solution. A peptide nanostructure was prepared through self-assembly.

Test Example 1

Circular dichroism (CD) spectroscopic analysis was performed as follows in order to investigate the dependence of the conformation of the amphiphilic peptide prepared in Preparation Example on ionic strength.

CD spectra were recorded using the Chirascan circular dichroism spectrometer equipped with a Peltier thermostat. The spectra were recorded between 260 nm and 190 nm using a 2-mm path cuvette. 10 scans were averaged. Also, molar ellipticity per amino acid residue was calculated. The peptide concentration was 1 μM unless specified otherwise and the sample solution incubated at least for a day before the measurement.

Figure 8:
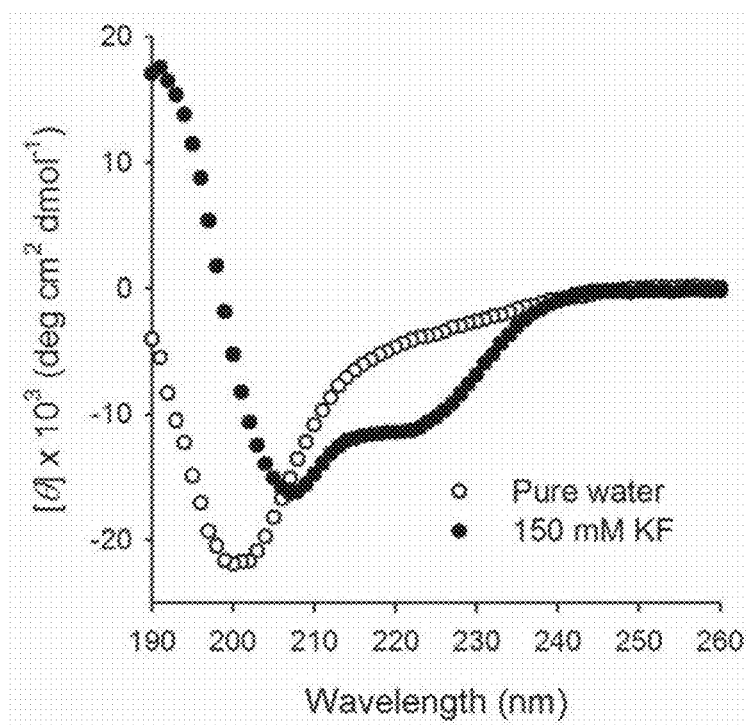
FIG. 8 shows a circular dichroism (CD) spectroscopic analysis result obtained after dissolving an amphiphilic peptide prepared in Preparation Example in water or a 150 mM KF solution to investigate the dependence of the conformation of an amphiphilic peptide of the present disclosure on ionic strength.

FIG. 8 shows the circular dichroism (CD) spectroscopic analysis result obtained after dissolving the amphiphilic peptide prepared in Preparation Example in water or a 150 mM KF solution to investigate the dependence of the conformation of the amphiphilic peptide of the present disclosure on ionic strength. In the graph, ○ indicates the peptide dissolved in water, and • indicates the peptide dissolved in 150 mM KF. In Test Example 1, the measurement of the samples was measured at 4° C.

As seen from FIG. 8, it was found that the molar ellipticity at 208 nm and 222 nm increased as the ionic strength was increased to 150 mM. For comparison of the CD analysis result, the ratio of the ellipticity at 208 nm and the ellipticity at 222 nm, $[\theta]_{222}/[\theta]_{208}$, was calculated. The $[\theta]_{222}/[\theta]_{208}$ is sensitive to the backbone dihedral angle and can be used as a measure of the degree of α-helix stabilization. The $[\theta]_{222}/[\theta]_{208}$ was measured to be higher when the ionic strength was increased (0.71) as compared to in water (0.31).

Figure 9:
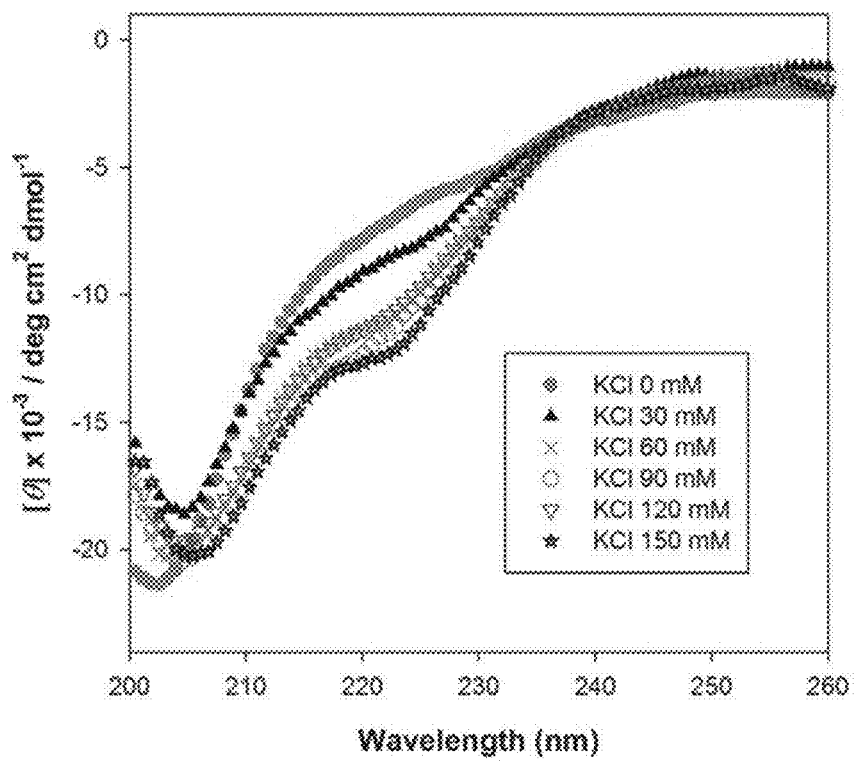
FIG. 9 shows a circular dichroism (CD) spectroscopic analysis result of an amphiphilic peptide prepared in Preparation Example depending on ionic strength. Samples were prepared by dissolving 1 μM of the amphiphilic peptide in HEPES buffer with different KCl concentrations.

FIG. 9 shows the circular dichroism (CD) spectroscopic analysis result of the amphiphilic peptide prepared in Preparation Example depending on ionic strength. The samples were prepared by dissolving 1 μM of the amphiphilic peptide in HEPES buffer with different KCl concentrations.

As seen from FIG. 9, the $[\theta]_{222}/[\theta]_{208}$, which is a measure of the degree of α-helix stabilization, increased as the ionic strength was increased gradually.

From FIG. 8 and FIG. 9, it was found out that the amphiphilic peptide prepared in Preparation Example could not form a self-assembled peptide nanostructure when dissolved in water. In contrast, as the ionic strength was increased, the self-assembled peptide nanostructure was formed due to increased hydrophobic interaction and increased helicity of the α-helical secondary structure as a result thereof.

To conclude, it was confirmed that, under a high ionic strength condition, enhanced hydrophobic interaction inside and outside the V-shaped hairpin dimer affects the conformation of the self-assembled peptide nanostructure and the binding of the self-assembled peptide nanostructure to the target substance under such an ionic strength can provide a more dynamic structure.

Figure 10A:
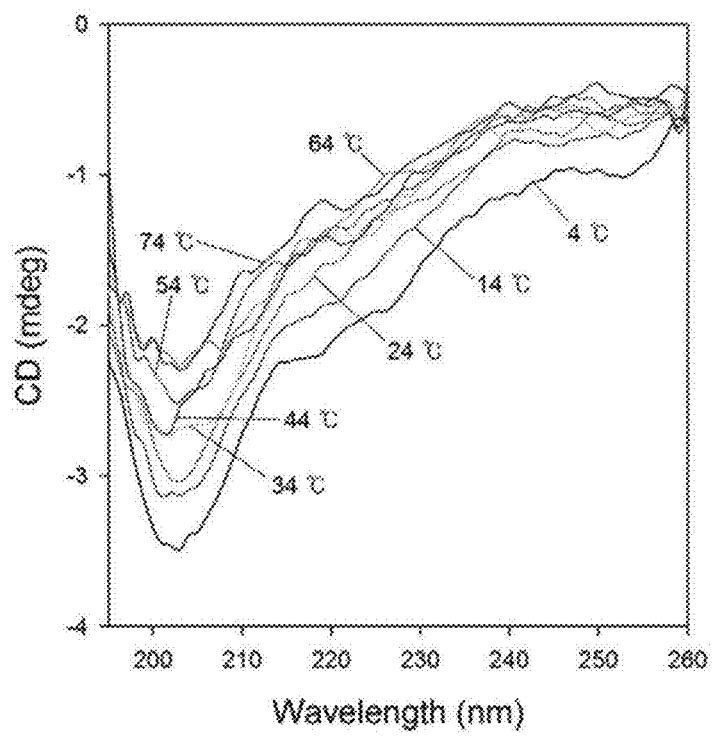
FIG. 10a, FIG. 10b and FIG. 10c respectively show a circular dichroism (CD) spectroscopic analysis result of an amphiphilic peptide prepared in Preparation Example in 0, 75 and 150 mM KCl solutions at various temperatures.
Figure 10B:
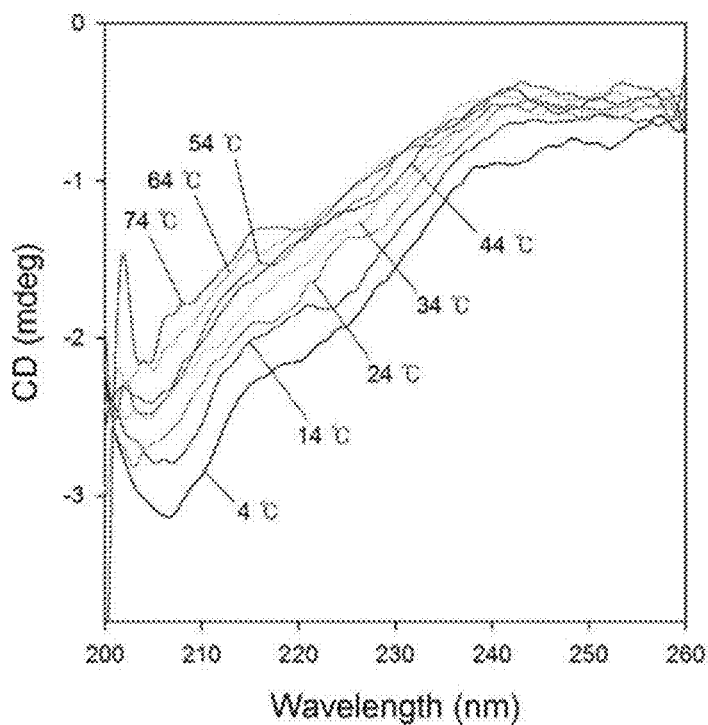
Figure 10C:
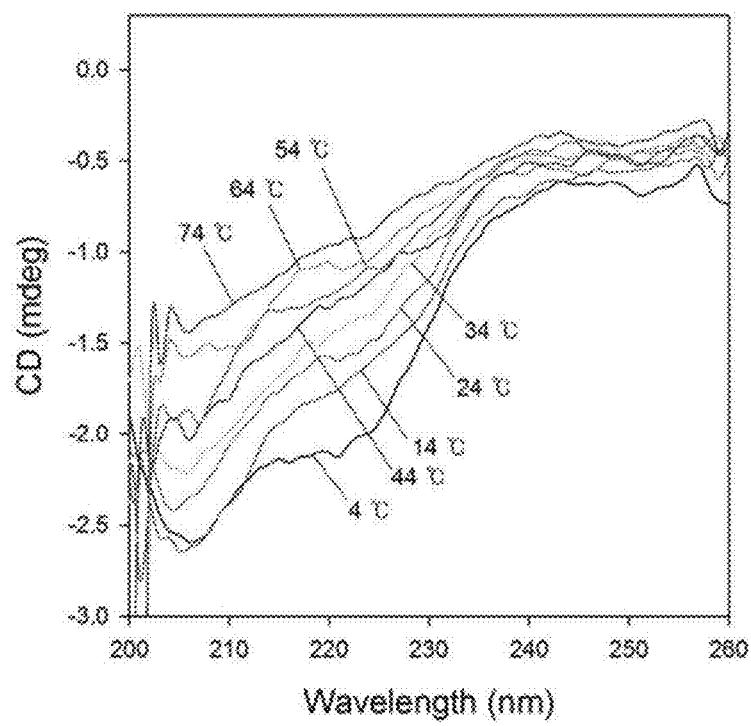

FIG. 10a, FIG. 10b and FIG. 10c respectively show the circular dichroism (CD) spectroscopic analysis result of the amphiphilic peptide prepared in Preparation Example in 0, 75 and 150 mM KCl solutions at various temperatures.

Figure 11A:
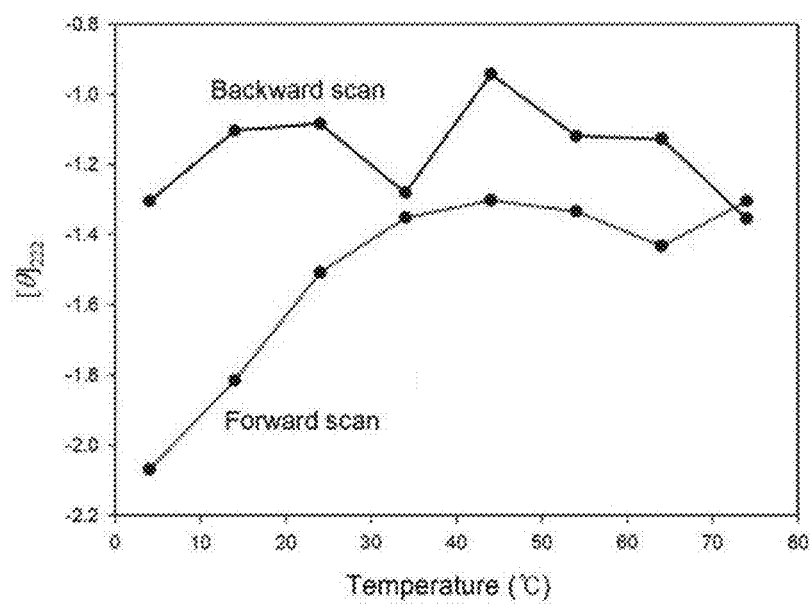
FIG. 11a, FIG. 11b and FIG. 11c show molar ellipticity at 222 nm ($[\theta]_{222}$) of FIG. 10a, FIG. 10b and FIG. 10c at various temperatures.
Figure 11B:
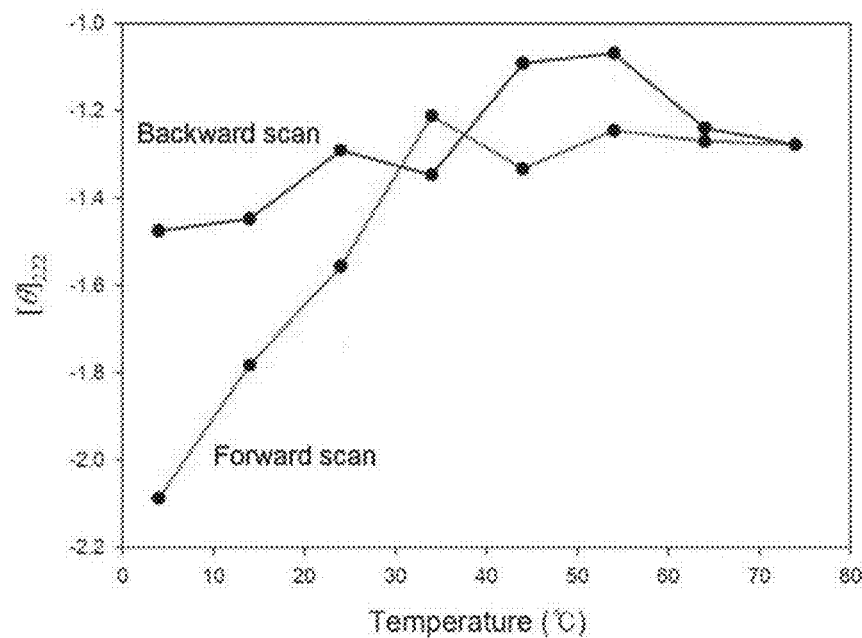
Figure 11C:
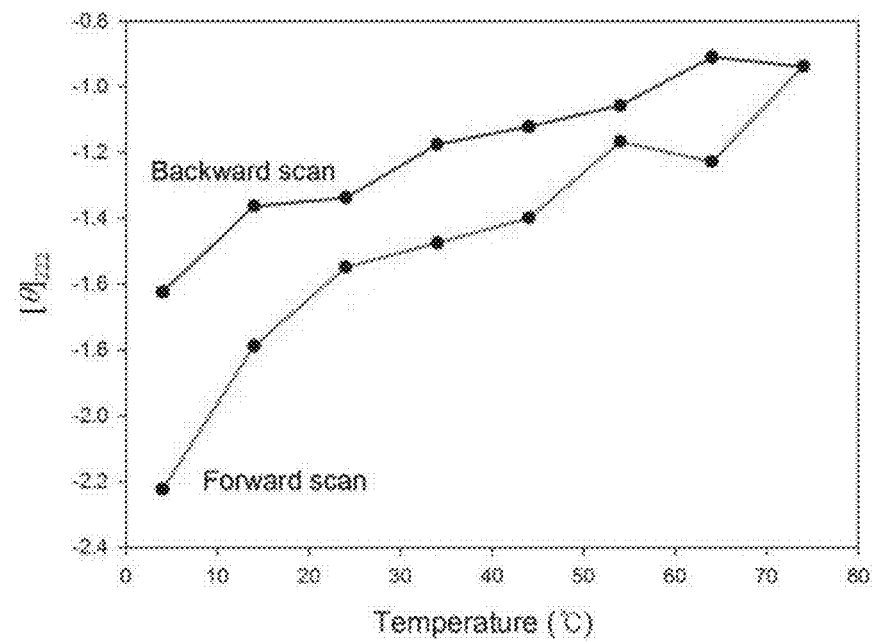

FIG. 11a, FIG. 11b and FIG. 11c show the molar ellipticity at 222 nm ($[\theta]_{222}$) of FIG. 10a, FIG. 10b and FIG. 10c at various temperatures.

From FIGS. 10a-10c and FIGS. 11a-11c, it can be seen that the amphiphilic peptide according to the present disclosure is affected by temperature change at each ionic strength.

Figure 12:
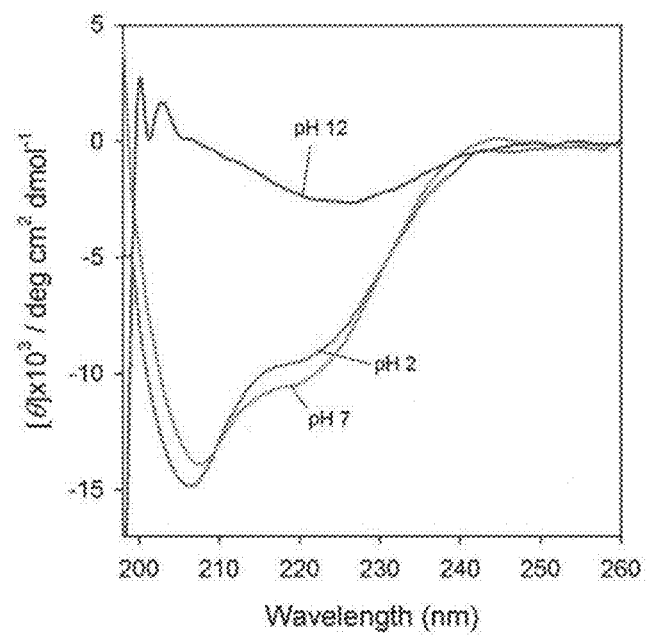
FIG. 12 shows a circular dichroism (CD) spectroscopic analysis result showing the effect of pH on the structure of an amphiphilic peptide according to the present disclosure prepared in Preparation Example.

FIG. 12 shows the circular dichroism (CD) spectroscopic analysis result showing the effect of pH on the structure of the amphiphilic peptide according to the present disclosure prepared in Preparation Example.

From FIG. 12, it can be seen that solubility decreases gradually as the pH increases. This is because the amino acid residues constituting the amphiphilic peptide such as lysine and arginine are deprotonated.

From FIGS. 10a-10c, FIGS. 11a-11c and FIG. 12, it can be seen that the structural stabilization of the amphiphilic peptide according to the present disclosure is affected not only by the ionic strength but also by the temperature and pH.

Test Example 2

The amphiphilic peptide prepared in Preparation Example was subjected to fluorescence spectroscopic measurement after dissolving in water or a 150 mM KF solution. Details are as follows.

Figure 13:
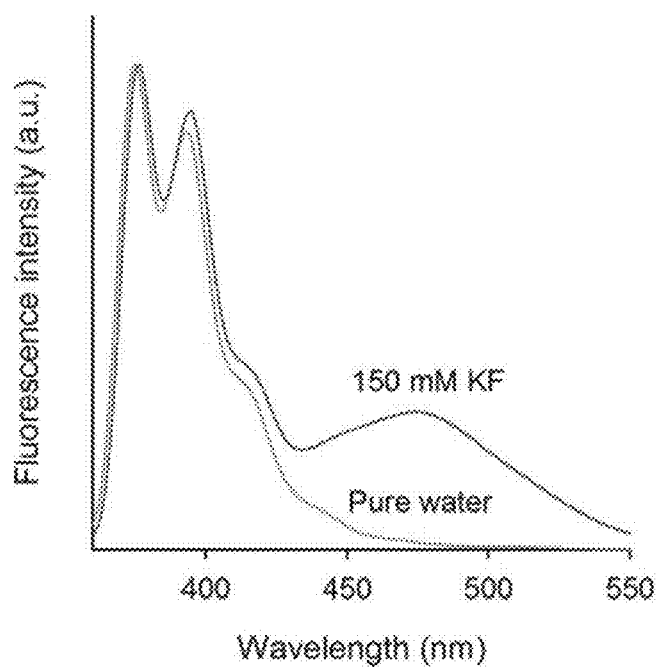
FIG. 13 shows fluorescence emission spectra of an amphiphilic peptide prepared in Preparation Example obtained after dissolving in water and a 150 mM KF solution, respectively.

Fluorescence spectra were measured using the LS55 fluorescence spectrometer (PerkinElmer). Pyrene was excited at 341 nm and the emission spectra were recorded in the range of 360-550 nm. The result is shown in FIG. 13. The solid (-) curve indicates the amphiphilic peptide dissolved in 150 mM KF and the dotted ( . . . ) curve indicates the amphiphilic peptide dissolved in water.

Also, emission spectra were measured after dissolving 0.25-20 μM of the amphiphilic peptide prepared in Preparation Example in water (a) or a KF solution (b). The result is shown in FIG. 14.

Figure 14:
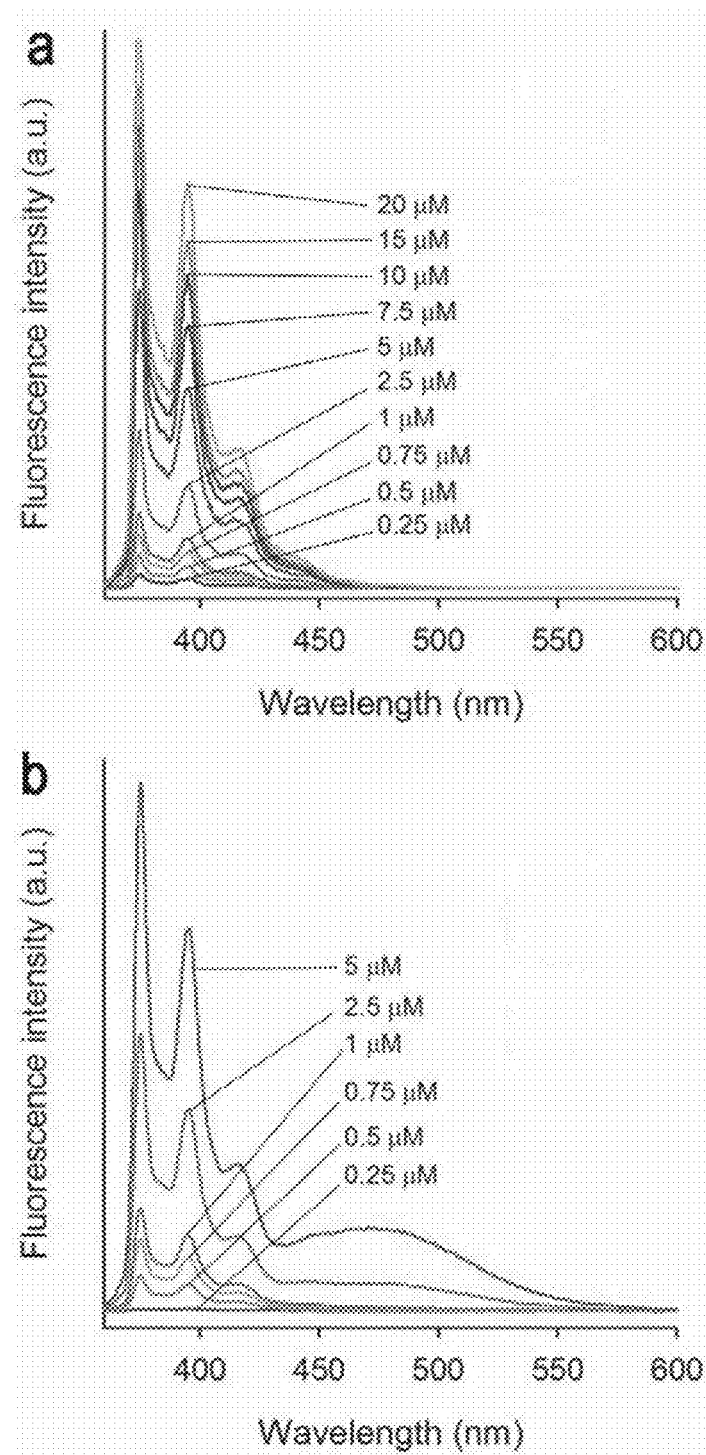
FIG. 14 shows fluorescence emission spectra of 0.25-20 μM of an amphiphilic peptide prepared in Preparation Example obtained after dissolving in water and a 150 mM KF solution, respectively.

As seen from FIG. 13 and FIG. 14, the peaks with fluorescence intensity characteristic of an excimer were observed under a high ionic strength condition. This indicates that the amphiphilic peptide prepared in Preparation Example was self-assembled to form a peptide nanostructure and, as a result thereof, an excimer was formed due to the decreased spatial distance between the pyrene groups of adjacent amphiphilic peptides.

That is to say, when the amphiphilic peptide prepared in Preparation Example was dissolved in pure water (FIG. 14a), no excimer peak of pyrene was observed because the peptide nanostructure was not formed by self-assembly even at the high peptide concentration. In contrast, when the ionic strength was increased to 150 mM (FIG. 14b), the excimer peak of pyrene was observed because the peptide nanostructure was formed from self-assembly of the amphiphilic peptide.

In addition, it was confirmed from FIG. 14b that the fluorescence intensity of the self-assembled peptide nanostructure increases with the concentration of the amphiphilic peptide.

Test Example 3

The amphiphilic peptide prepared in Preparation Example was subjected to atomic force microscopic (AFM) measurement. Atomic force microscopic scanning was made at 1.2-1.5 V with 0.5 Hz. The result is shown in FIGS. 15a-15b and FIGS. 16a-16b.

Figure 15A:
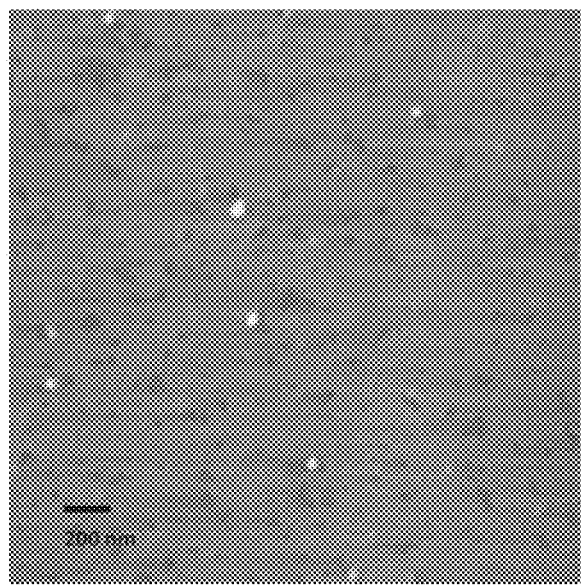
FIGS. 15a and 15b show atomic force microscopic (AFM) images of 2.5 μM of an amphiphilic peptide dissolved in water.
Figure 15B:
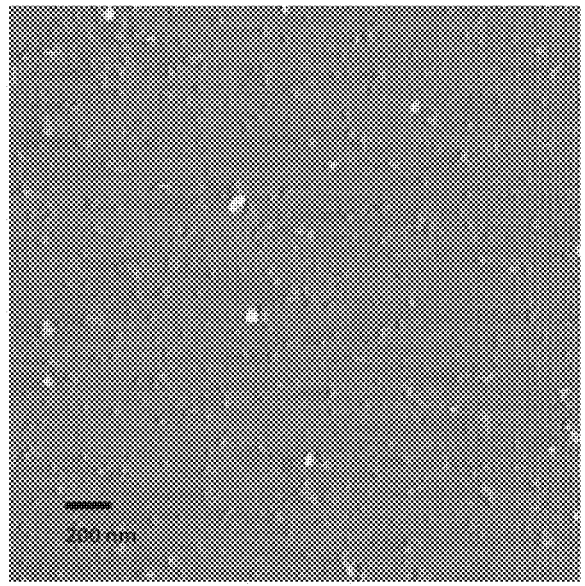

FIGS. 15a and 15b show atomic force microscopic (AFM) images of 2.5 μM of the amphiphilic peptide dissolved in water. FIG. 15a is a height image and FIG. 15b is a phase image.

Figure 16A:
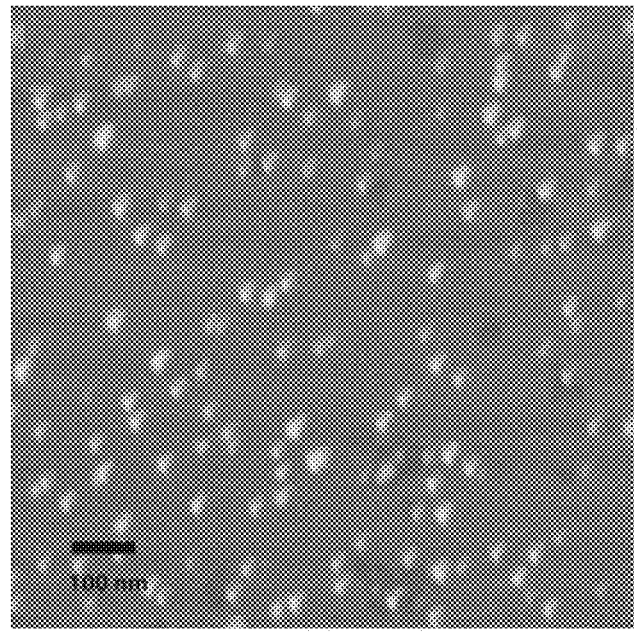
FIGS. 16a and 16b show atomic force microscopic (AFM) images of 1 μM of an amphiphilic peptide dissolved in a 150 mM KF solution.
Figure 16B:
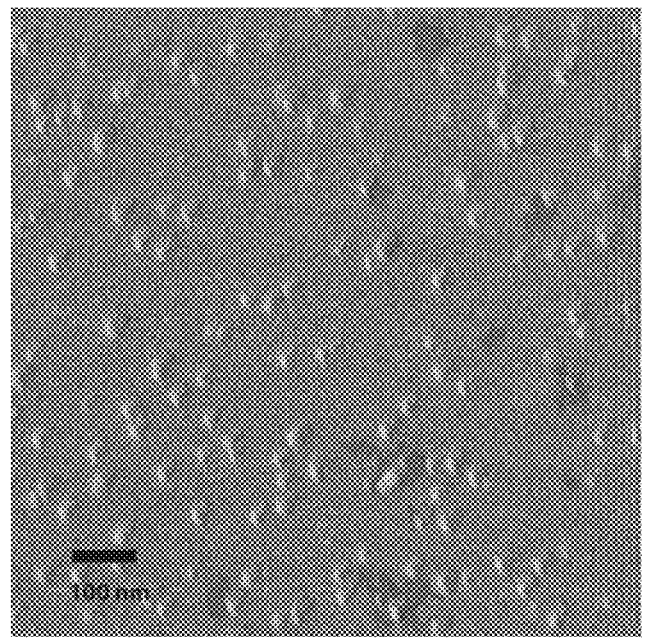

FIGS. 16a and 16b show atomic force microscopic (AFM) images of 1 μM of the amphiphilic peptide dissolved in a 150 mM KF solution. FIG. 16a is a height image and FIG. 16b is a phase image.

It can be seen from FIGS. 15a and 15b that the amphiphilic peptide dissolved in water exists mostly in monomer form. And, it can be seen from FIGS. 16a and 16b that globular nanostructures having a particle diameter of 20-50 nm are formed under high ionic strength. This suggests that the self-assembled peptide nanostructure according to the present disclosure exists only under a high ionic strength condition.

Test Example 4

Figure 17:
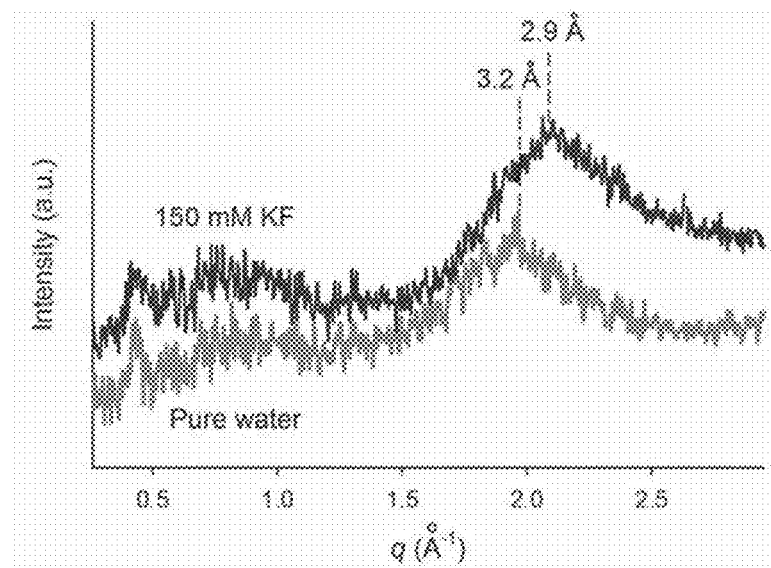
FIG. 17 shows a wide-angle X-ray scattering (WAXS) analysis result of an amphiphilic peptide prepared in Preparation Example to investigate the conformational change of the amphiphilic peptide depending on ionic strength.

FIG. 17 shows a wide-angle X-ray scattering (WAXS) analysis result of the amphiphilic peptide prepared in Preparation Example to investigate the conformational change of the amphiphilic peptide depending on ionic strength. The blue curve indicates the amphiphilic peptide prepared in Preparation Example dissolved in a 150 mM KF solution, and the green curve indicates that dissolved in water (distilled water).

From FIG. 17, it can be clearly seen that the amphiphilic peptide prepared in Preparation Example forms the peptide nanostructure through self-assembly under high ionic strength. That is to say, the increased ionic strength leads to conformational change through the self-assembly of the amphiphilic peptide prepared in Preparation Example and the stabilization of the secondary structure (helical structure).

Test Example 5

The self-assembled peptide nanostructure prepared in Example includes the amino acid sequence derived from the HIV-1 rev protein. It recognizes and binds to HIV-1 RRE RNA. In particular, the stem-loop II in RRE RNA (hereinafter, also referred to as IIB RNA) is essential for the recognition of HIV-1 RRE RNA by the rev protein.

In order to investigate the structure of the self-assembled peptide nanostructure prepared in Example before and after mixing with IIB RNA, circular dichroism (CD) spectroscopic analysis was conducted under the same condition as in Test Example 1. The result is shown in FIG. 18, wherein ● indicates after mixing with IIB RNA and ○ indicates before mixing with IIB RNA.

Figure 18:
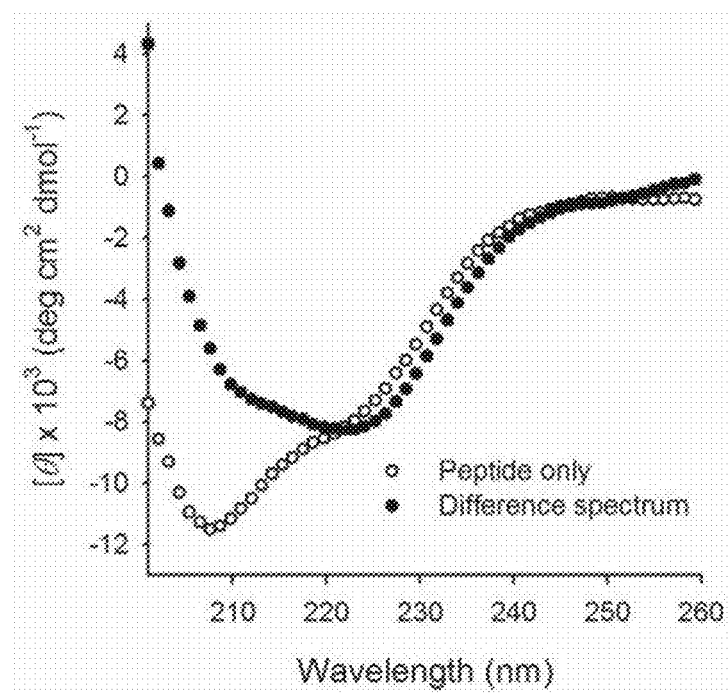
FIG. 18 shows a circular dichroism (CD) spectroscopic analysis result of a self-assembled peptide nanostructure prepared in Example before and after mixing with IIB RNA.

As seen from FIG. 18, before mixing with IIB RNA, the self-assembled peptide nanostructure prepared in Example showed moderate stabilization degree of the secondary structure (α-helical structure) with the $[\theta]_{222}/[\theta]_{208}$ value of 0.65. In contrast, after mixing with IIB RNA, the secondary structure (α-helical structure) of the self-assembled peptide nanostructure prepared in Example was significantly stabilized with the $[\theta]_{222}/[\theta]_{208}$ value of 1.15.

For more accurate comparison, the result for IIB RNA was excluded from the result for the self-assembled peptide nanostructure prepared in Example after mixing with IIB RNA. As a result, it was confirmed that the binding between IIB RNA and the self-assembled peptide nanostructure leads to the conformational change of the secondary structure (helical structure) according to the induced fit model. This explains why the overall size of the self-assembled peptide nanostructure is increased after binding with IIB RNA while maintaining the globular shape.

Test Example 6

In order to investigate the structure of the self-assembled peptide nanostructure prepared in Example before and after mixing with IIB RNA, atomic force microscopic (AFM) measurement was made under the same condition as in Test Example 3. The result is shown in FIGS. 19a-19b and FIGS. 20a-20b.

Figure 19A:
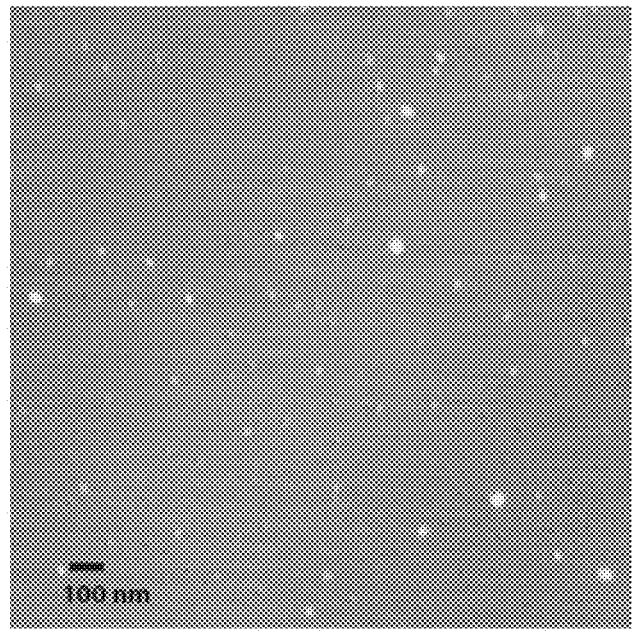
FIGS. 19a and 19b show atomic force microscopic (AFM) images of a self-assembled peptide nanostructure prepared in Example before mixing with IIB RNA.
Figure 19B:
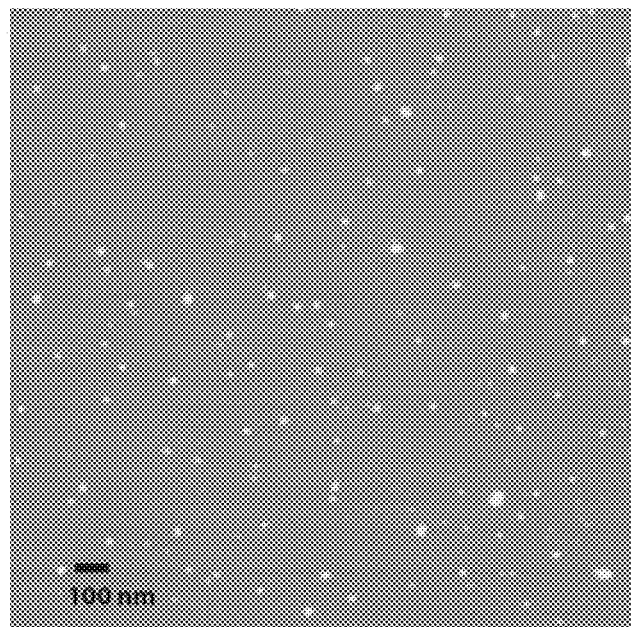

FIGS. 19a and 19b show atomic force microscopic (AFM) images of the self-assembled peptide nanostructure prepared in Example before mixing with IIB RNA. FIG. 19a is a height image and FIG. 19b is a phase image.

Figure 20A:
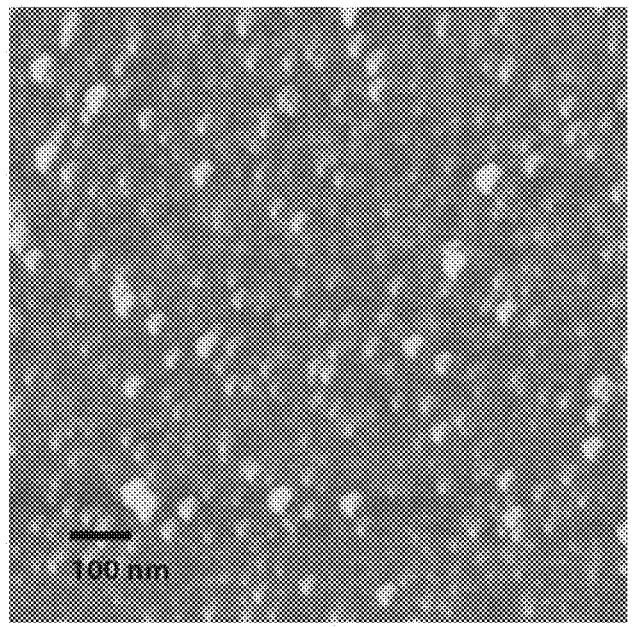
FIGS. 20a and 20b show atomic force microscopic (AFM) images of a self-assembled peptide nanostructure prepared in Example after mixing with IIB RNA.
Figure 20B:
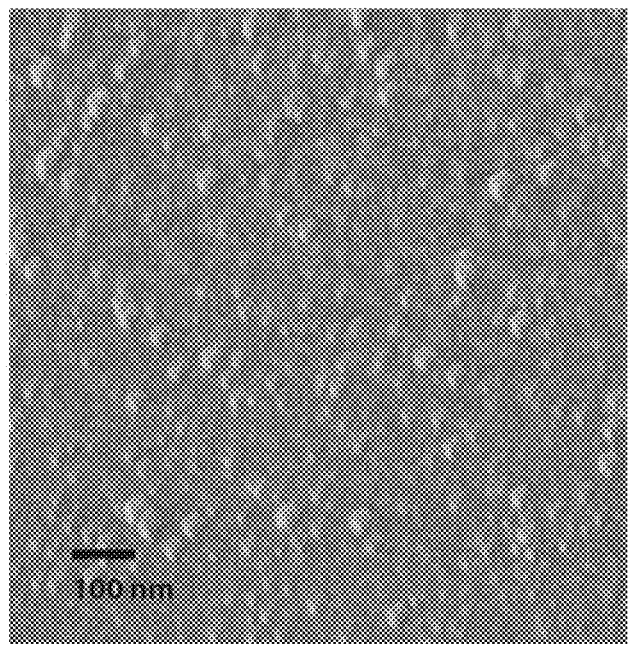

FIGS. 20a and 20b show atomic force microscopic (AFM) images of the self-assembled peptide nanostructure prepared in Example after mixing with IIB RNA. FIG. 20a is a height image and FIG. 20b is a phase image.

As seen from FIGS. 19a-19b and FIGS. 20a-20b, the self-assembled peptide nanostructure according to the present disclosure maintains the globular shape after binding with IIB RNA although the overall size was increased.

Test Example 7

In order to investigate whether the self-assembled peptide nanostructure of the present disclosure can detect a target substance, fluorescence spectroscopic analysis was conducted under the same condition as in Test Example 2 before and after mixing the self-assembled peptide nanostructure prepared in Example (1 μM) with IIB RNA (0.5 μM). The result is shown in FIG. 21, wherein the lighter colored curve indicates after mixing with IIB RNA and the darker colored curve indicates before mixing with IIB RNA.

Figure 21:
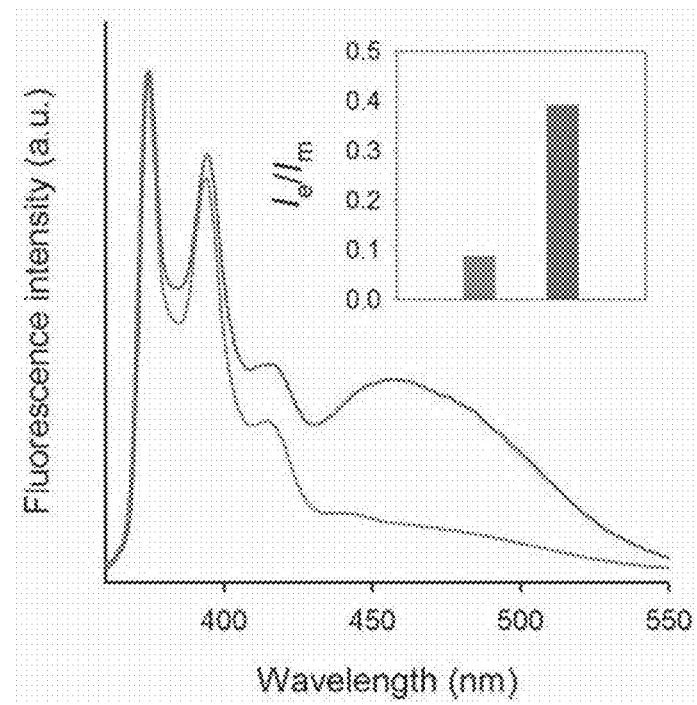
FIG. 21 shows a fluorescence spectroscopic analysis result of a self-assembled peptide nanostructure prepared in Example (1 μM) before and after mixing with IIB RNA (0.5

As seen from FIG. 21, the self-assembled peptide nanostructure prepared in Example showed increased fluorescence intensity after mixing with IIB RNA. This suggests that the recognition of and binding to IIB RNA by the self-assembled peptide nanostructure prepared in Example led to conformational change and, as a result, an excimer was formed due to the decreased distance between the pyrene groups of adjacent amphiphilic peptides in the self-assembled peptide nanostructure.

The fluorescence emission was observed under an increased ionic strength condition.

To quantify the result of FIG. 21, the ratio of fluorescence intensities at different wavelengths was calculated and the result is shown in the insert of FIG. 21. $I_m$ indicates the fluorescence intensity of the pyrene monomer at 373 nm and $I_e$ indicates the fluorescence intensity of the pyrene dimer (in excimer form) at 480 nm.

Test Example 8

The selectivity for a specific target substance, which is the essential factor required for the self-assembled peptide nanostructure prepared in Example to be used as a biosensor, was investigated.

For this, single-stranded DNA (ssDNA; T7 DNA), wild-type IIB RNA (RRE WT; HIV-1 RRE RNA), mutated IIB RNA (modification from G46-C74 to C46-G74; RRE MT; HIV-1 RRE RNA variant) and tRNA were respectively mixed with the self-assembled peptide nanostructure prepared in Example and fluorescence spectroscopic analysis was conducted under the same condition as in Test Example 2. The result is shown in FIG. 22a. FIG. 22b shows the ratiometric fluorescence determined from FIG. 22a.

As seen from FIG. 22, the lowest fluorescence intensity was observed when there was the self-assembled peptide nanostructure prepared in Example only, and the highest fluorescence intensity was observed when it was mixed with wild-type IIB RNA.

In addition, fluorescence intensities were different for the different polynucleotides (ssDNA, tRNA, RRE MT and RRE WT). This suggests that the self-assembled peptide nanostructure according to the present disclosure can be used to detect specific target substances.

In particular, it is to be noted that it can distinguish wild-type IIB RNA (RRE RNA WT) from mutated IIB RNA (RRE MT).

Test Example 9

In order to investigate the importance of ionic strength in the use of the self-assembled peptide nanostructure prepared in Example as a biosensor, selectivity for specific target substances was investigated under different ionic strength conditions.

For this, single-stranded DNA (ssDNA; T7 DNA), wild-type IIB RNA (RRE WT; HIV-1 RRE RNA), mutated IIB RNA (modification from G46-C74 to C46-G74; RRE MT; HIV-1 RRE RNA variant) and tRNA were respectively mixed with the self-assembled peptide nanostructure prepared in Example and fluorescence spectroscopic analysis was conducted under the same condition as in Test Example 8. The result is shown in FIGS. 23a-23c.

FIG. 23a shows the selectivity of the self-assembled peptide nanostructure prepared in Example for different biomolecules at 0 mM KCl, FIG. 23b shows the selectivity of the self-assembled peptide nanostructure prepared in Example for different biomolecules at 30 mM KCl, and FIG. 23c shows the selectivity of the self-assembled peptide nanostructure prepared in Example for different biomolecules at 150 mM KCl.

From FIGS. 23a-23c, it can be seen that the self-assembled peptide nanostructure prepared in Example exhibits superior selectivity as a biosensor under a high ionic strength condition (FIG. 23c).

This suggests that ionic strength affects the selectivity of the biosensor according to the present disclosure and that the biosensor has excellent detection sensitivity and selectivity for target substances under the ionic strength of 0.1-0.3 M.

---

What is claimed is:

1. A self-assembled peptide nanostructure comprising at least one amphiphilic peptide, wherein the amphiphilic peptide comprises a first hydrophobic oligomerization domain, a hydrophilic α-helix domain and a second hydrophobic oligomerization domain sequentially from the N-terminal to the C-terminal, and the N-terminal of the first hydrophobic oligomerization domain is a pyrene group,
wherein the hydrophilic α-helix domain comprises an arginine-rich motif (ARM) and a proline-rich loop forming an α-helical structure,
wherein the arginine-rich motif comprises an amino acid sequence of [SEQ ID NO 1]:

[SEQ ID NO 1]
TRQARRNRRRRWERQR wherein the proline-rich loop comprises an amino acid sequence of [SEQ ID NO 2]:

[SEQ ID NO 2]
GEPNPPP; and wherein the first and second hydrophobic oligomerization domains respectively comprise an amino acid sequence of [SEQ ID NO 3] and [SEQ ID NO 4]:

QIHSISERILSTYLK [SEQ ID NO 3]

NSQYLFKILRVAKLL. [SEQ ID NO 4]

2. The self-assembled peptide nanostructure according to claim 1, wherein the amphiphilic peptide is a hairpin-shaped amphiphilic peptide wherein the first and second hydrophobic oligomerization domains are bound to each other.

3. The self-assembled peptide nanostructure according to claim 2, wherein the peptide nanostructure is formed as a globular peptide nanostructure from self-assembly of the hairpin-shaped amphiphilic peptide.

4. The self-assembled peptide nanostructure according to claim 1, wherein the peptide nanostructure has an average particle diameter of 20-70 nm.

5. The self-assembled peptide nanostructure according to claim 1, wherein the arginine-rich motif is derived from the 34th through 50th amino acid sequence of the HIV-1 rev protein.

6. The self-assembled peptide nanostructure according to claim 1, wherein the first and second hydrophobic oligomerization domains are derived respectively from the 9th through 26th or 51st through 65th amino acid sequence of the HIV-1 rev protein.

7. The self-assembled peptide nanostructure according to claim 1, wherein the peptide nanostructure maintains the shape of the peptide nanostructure from self-assembly of the amphiphilic peptide when the ionic strength is 0.1-0.3 M.

8. The self-assembled peptide nanostructure of claim 1, wherein the amphiphilic peptide comprises an amino acid sequence of [SEQ ID NO: 8].

9. A biosensor comprising the self-assembled peptide nanostructure according to claim 8.

10. The biosensor according to claim 9, wherein the self-assembled peptide nanostructure has a stabilized (folded) α-helical structure after binding with a target substance and a light-emitting characteristic of the biosensor is changed depending on the distance between pyrene groups of each amphiphilic peptide in the stabilized self-assembled peptide nanostructure.

11. The biosensor according to claim 9, wherein the biosensor detects a target substance under an ionic strength of 0.1-0.3 M.

12. The biosensor according to claim 11, wherein the target substance is selected from a group consisting of an amino acid, a protein, an RNA and a DNA.

13. The biosensor according to claim 11, wherein the target substance is HIV-1 RRE RNA.

14. A detection method using a biosensor, comprising:
I) contacting a sample comprising a target substance with the biosensor according to claim 9; and
II) detecting the target substance by measuring the fluorescence intensity of the biosensor.

* * * * *

SEQUENCE LISTING

```
<160> NUMBER OF SEQ ID NOS: 8

<210> SEQ ID NO 1
<211> LENGTH: 16
<212> TYPE: PRT
<213> ORGANISM: Human immunodeficiency virus 1

<400> SEQUENCE: 1

Thr Arg Gln Ala Arg Arg Asn Arg Arg Arg Arg Trp Glu Arg Gln Arg
1               5                   10                  15

<210> SEQ ID NO 2
<211> LENGTH: 7
<212> TYPE: PRT
<213> ORGANISM: Human immunodeficiency virus 1

<400> SEQUENCE: 2

Gly Glu Pro Asn Pro Pro Pro
1               5

<210> SEQ ID NO 3
<211> LENGTH: 15
<212> TYPE: PRT
<213> ORGANISM: Human immunodeficiency virus 1

<400> SEQUENCE: 3

Gln Ile His Ser Ile Ser Glu Arg Ile Leu Ser Thr Tyr Leu Lys
1               5                   10                  15

<210> SEQ ID NO 4
<211> LENGTH: 15
```

```
<212> TYPE: PRT
<213> ORGANISM: Human immunodeficiency virus 1

<400> SEQUENCE: 4

Asn Ser Gln Tyr Leu Phe Lys Ile Leu Arg Val Ala Lys Leu Leu
1               5                   10                  15

<210> SEQ ID NO 5
<211> LENGTH: 44
<212> TYPE: RNA
<213> ORGANISM: Human immunodeficiency virus 1

<400> SEQUENCE: 5
gaccugguau gggcgcagcg caagcugacg guacaggcca gguc              44

<210> SEQ ID NO 6
<211> LENGTH: 44
<212> TYPE: RNA
<213> ORGANISM: Human immunodeficiency virus 1

<400> SEQUENCE: 6
gaccugguau cggcgcagcg caagcugacg guagaggcca gguc              44

<210> SEQ ID NO 7
<211> LENGTH: 25
<212> TYPE: DNA
<213> ORGANISM: Enterobacteria phage T7

<400> SEQUENCE: 7
taatacgact cactatagga cctgg                                   25

<210> SEQ ID NO 8
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Leu Lys Ala Val Arg Leu Ile Lys Phe Leu Tyr Gln Ser Asn Pro
1               5                   10                  15

Pro Pro Asn Pro Glu Gly Thr Arg Gln Ala Arg Arg Asn Arg Arg Arg
            20                  25                  30

Arg Trp Arg Glu Arg Gln Arg Gln Ile His Ser Ile Ser Glu Arg Ile
        35                  40                  45

Leu Ser Thr Tyr Leu Lys
    50
```